US012561806B2

(12) United States Patent
Defresne et al.

(10) Patent No.: US 12,561,806 B2
(45) Date of Patent: Feb. 24, 2026

(54) COMPUTE SYSTEM WITH EXPLAINABLE AI FOR SKIN LESIONS ANALYSIS MECHANISM AND METHOD OF OPERATION THEREOF

(71) Applicant: BelleTorus Corporation, Cambridge, MA (US)

(72) Inventors: Marianne Alix Delphine Defresne, Toulouse (FR); Élise Coutier, Saint Sébastien sur Loire (FR); Paul Fricker, Toulouse (FR); Folkert Blok, Toulouse (FR); Thi Thu Hang Nguyen, Toulouse (FR)

(73) Assignee: BelleTorus Corporation, Cambridge, MA (US)

( * ) Notice: Subject to any disclaimer, the term of this patent is extended or adjusted under 35 U.S.C. 154(b) by 0 days.

(21) Appl. No.: 18/883,934

(22) Filed: Sep. 12, 2024

(65) Prior Publication Data

US 2025/0322511 A1 Oct. 16, 2025

Related U.S. Application Data

(60) Provisional application No. 63/634,126, filed on Apr. 15, 2024.

(51) Int. Cl.
*G06T 7/00* (2017.01)
*G06T 7/10* (2017.01)
*G16H 50/30* (2018.01)

(52) U.S. Cl.
CPC .............. *G06T 7/0012* (2013.01); *G06T 7/10* (2017.01); *G16H 50/30* (2018.01);
(Continued)

(58) Field of Classification Search
None
See application file for complete search history.

(56) References Cited

U.S. PATENT DOCUMENTS 8,224,427 B2 7/2012 Kopriva
8,849,380 B2 9/2014 Patwardhan
(Continued)

OTHER PUBLICATIONS

Maqsood, Sarmad, and Robertas DamaÅ¡eviÄ¡ius "Multiclass skin lesion localization and classification using deep learning based features fusion and selection framework for smart healthcare." Neural networks 160 (2023): 238-258. (Year: 2023).*
(Continued)

*Primary Examiner* — Samah A Beg
(74) *Attorney, Agent, or Firm* — Perspectives Law Group, Corp.

(57) ABSTRACT

A method of operation of a compute system includes: segmenting a skin lesion in a patient image; constructing a normalized image by cropping the patient image and adding padding to position the skin lesion at a center of the normalized image, identifying a skin lesion classification, a skin lesion sub-class, and a risk level assessment by analyzing a symmetry axis, a border, color variation, and dermoscopic structures, and generating a skin lesion display including the normalized image, the skin lesion classification, the skin lesion sub-class, and the risk level assessment for displaying on a device.

20 Claims, 19 Drawing Sheets
(16 of 19 Drawing Sheet(s) Filed in Color)

2700 —

SEGMENTING A SKIN LESION
2702

CONSTRUCTING A NORMALIZED IMAGE
2704

IDENTIFYING A SKIN LESION CLASSIFICATION
2706

GENERATING A SKIN LESION DISPLAY
2708

(52) U.S. Cl.
    CPC ............... *G06T 2207/20084* (2013.01); *G06T 2207/30088* (2013.01); *G06T 2207/30096* (2013.01)

(56) References Cited

U.S. PATENT DOCUMENTS

| | | | | |
|---|---|---|---|---|
| 10,335,190 | B2 | 7/2019 | Knowlton | |
| 11,244,456 | B2 * | 2/2022 | Kaffenberger | A61B 5/444 |
| 11,298,072 | B2 | 4/2022 | Dascalu | |
| 12,118,723 | B1 * | 10/2024 | Nguyen | G06V 10/764 |
| 2009/0137908 | A1 | 5/2009 | Patwardhan | |
| 2010/0130870 | A1 | 5/2010 | Kopriva | |
| 2012/0008838 | A1 * | 1/2012 | Guyon | G16H 50/20 |
| | | | | 382/128 |
| 2018/0235534 | A1 * | 8/2018 | Gareau | G06T 7/68 |
| 2018/0242993 | A1 | 8/2018 | Knowlton | |
| 2019/0290188 | A1 * | 9/2019 | Rundo | A61B 5/7264 |
| 2019/0336063 | A1 | 11/2019 | Dascalu | |
| 2022/0133215 | A1 * | 5/2022 | Mayer | G16H 30/40 |
| | | | | 600/477 |
| 2022/0172356 | A1 * | 6/2022 | Yang | G06N 3/045 |

OTHER PUBLICATIONS

Sankarapandian, Sivaramakrishnan, et al. "A pathology deep learning system capable of triage of melanoma specimens utilizing dermatopathologist consensus as ground truth." Proceedings of the IEEE/CVF international conference on computer vision. 2021. (Year: 2021).*

Talavera-Martínez, Lidia, et al. "A novel approach for skin lesion symmetry classification with a deep learning model." Computers in biology and medicine 145 (2022): 105450. (Year: 2022).*

Scebba, Gaetano, et al. "Detect-and-segment: A deep learning approach to automate wound image segmentation." Informatics in Medicine Unlocked 29 (2022): 100884. (Year: 2022).*

Jafari, Mohammad H., et al. "Automatic detection of melanoma using broad extraction of features from digital images." 2016 38th Annual International Conference of the IEEE Engineering in Medicine and Biology Society (EMBC). IEEE, 2016. (Year: 2016).*

Xie, Zhiqiang, et al. "Semi-supervised skin lesion segmentation with learning model confidence." ICASSP 2021-2021 IEEE International Conference on Acoustics, Speech and Signal Processing (ICASSP). IEEE, 2021. (Year: 2021).*

Ali, Abder-Rahman H., Jingpeng Li, and Guang Yang. "Automating the ABCD rule for melanoma detection: a survey." IEEE Access 8 (2020): 83333-83346. (Year: 2020).*

* cited by examiner

801

802

514

804

901

602

902

904

1301

ROC CURVES (AVG AUROC 0.924)

AK (AREA=0.95)
BCC (AREA=0.97)
BKL (AREA=0.94)
DF (AREA=0.97)
MEL (AREA=0.88)
NV (AREA=0.96)
OTHER (AREA=0.95)
SCC (AREA=0.95)
VASC (AREA=0.97)

TRUE POSITIVE RATE (SENSITIVITY)

FALSE POSITIVE RATE (1-SPECIFICITY)

1401

522 {
CANCER RISK LEVEL: 4
PREDICTION: RISK OF CANCER

520 {
PREFERENTIAL DX:
BCC: 1.0
BCC_PIGMENTED: 1.0
BCC_SUPERFICIAL: 0.96

1404 {
DIFFERENTIAL DX:
BCC_FEP: 0.23

602

1402

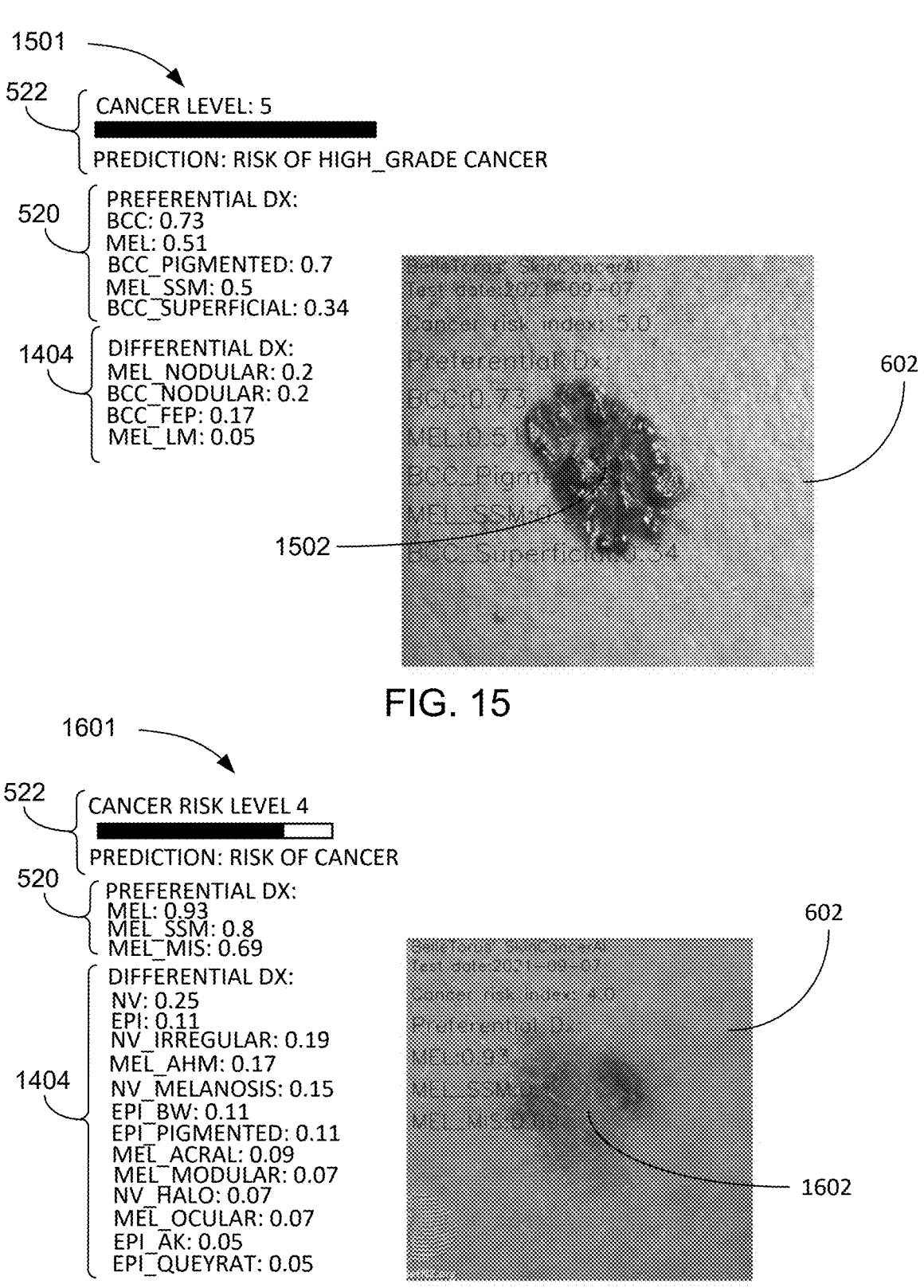

1501

522
CANCER LEVEL: 5

PREDICTION: RISK OF HIGH_GRADE CANCER

520
PREFERENTIAL DX:
BCC: 0.73
MEL: 0.51
BCC_PIGMENTED: 0.7
MEL_SSM: 0.5
BCC_SUPERFICIAL: 0.34

1404
DIFFERENTIAL DX:
MEL_NODULAR: 0.2
BCC_NODULAR: 0.2
BCC_FEP: 0.17
MEL_LM: 0.05

522
CANCER RISK LEVEL 4

PREDICTION: RISK OF CANCER

520
PREFERENTIAL DX:
MEL: 0.93
MEL_SSM: 0.8
MEL_MIS: 0.69

1404
DIFFERENTIAL DX:
NV: 0.25
EPI: 0.11
NV_IRREGULAR: 0.19
MEL_AHM: 0.17
NV_MELANOSIS: 0.15
EPI_BW: 0.11
EPI_PIGMENTED: 0.11
MEL_ACRAL: 0.09
MEL_MODULAR: 0.07
NV_HALO: 0.07
MEL_OCULAR: 0.07
EPI_AK: 0.05
EPI_QUEYRAT: 0.05

CANCER RISK LEVEL: 0

PREDICTION: CANCER SIGNS NOT FOUND

520

PREFERENTIAL DX:
BKL: 0.99
BKL_SK: 0.99

1404

DIFFERENTIAL DX:
BKL_LENTIGO: 0.07
BKL_SCALP: 0.07

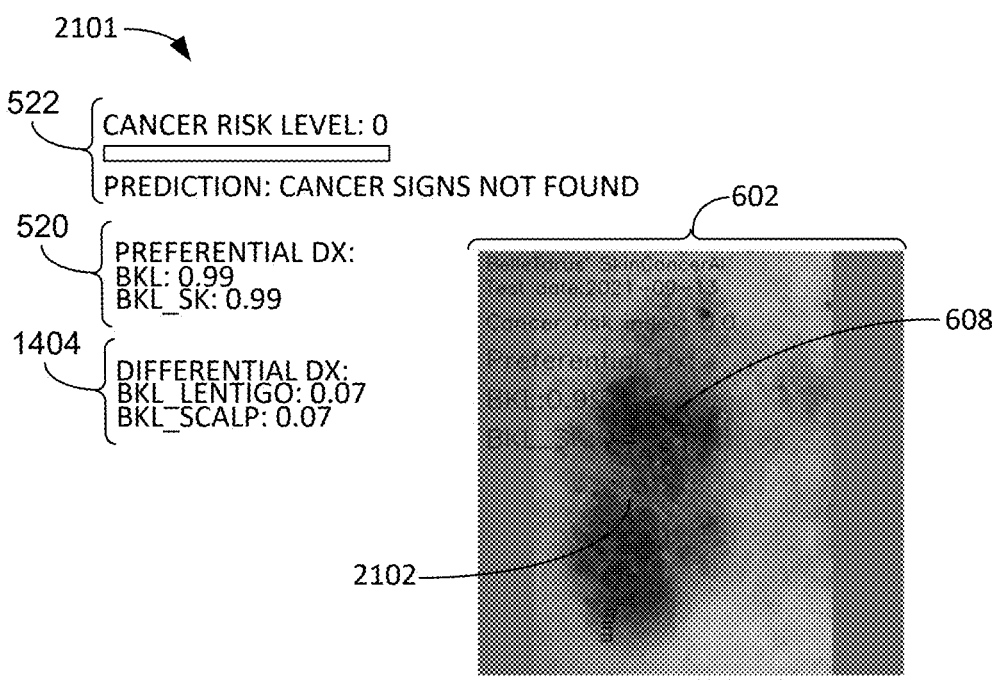

CANCER RISK LEVEL: 4

PREDICTION: RISK OF CANCER

520

PREFERENTIAL DX:
BCC: 0.69
MEL: 0.46
BCC_NODULAR: 0.61
BCC_AGGRESSIVE: 0.48
BCC_INFILTRATIVE: 0.47
MEL_AHM: 0.46
BCC_NONPIGMENTED: 0.39
MEL_SSM: 0.38
MEL_MIS: 0.33
BCC_SUPERFICIAL: 0.3

1404

DIFFERENTIAL DX:
BKL: 0.11
EPI: 0.11
BCC_ULCERATED: 0.2
MEL_LM: 0.12
BKL_SK: 0.1
BCC_MICRONODULAR: 0.1
EPI_BW: 0.1
MEL_NODULAR: 0.08
BKL_LPLK: 0.08
EPI_SCC: 0.07
BCC_PIGMENTED: 0.07

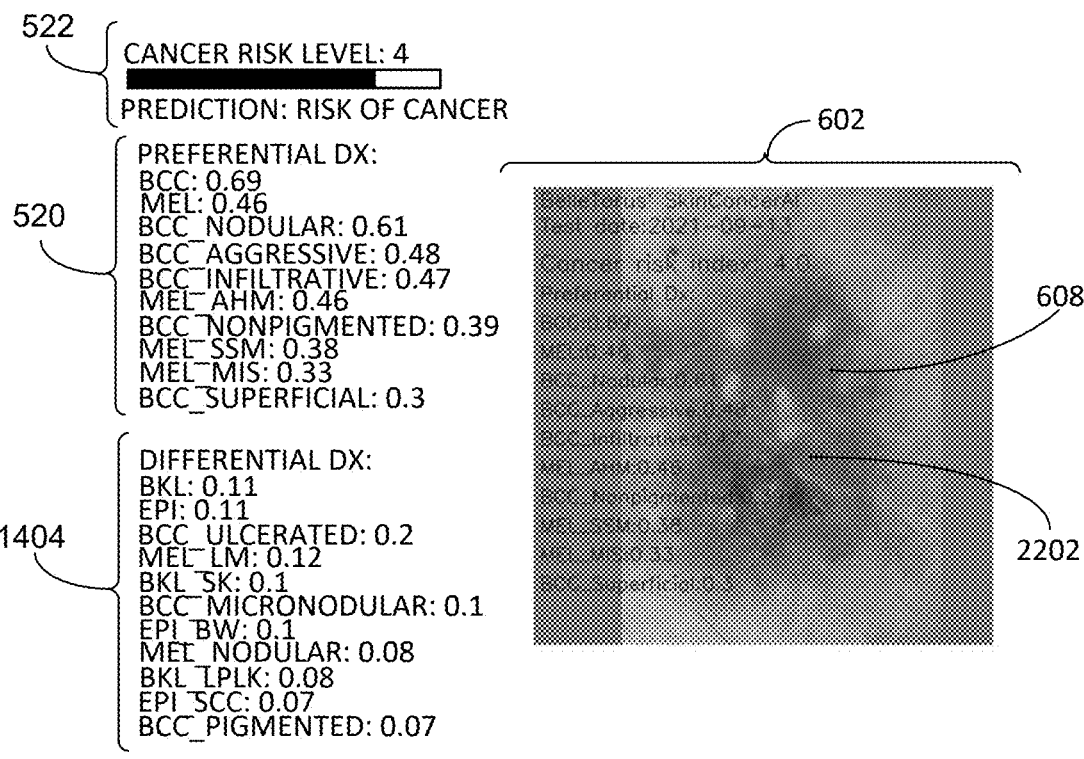

COMPUTE SYSTEM WITH EXPLAINABLE AI FOR SKIN LESIONS ANALYSIS MECHANISM AND METHOD OF OPERATION THEREOF

CROSS-REFERENCE TO RELATED APPLICATION

This application claims the benefit of U.S. Provisional Patent Application Ser. No. 63/634,126 filed Apr. 15, 2024, and the subject matter thereof is incorporated herein by reference thereto.

TECHNICAL FIELD

An embodiment of the present invention relates generally to a compute system, and more particularly to a system with an image based skin cancer detection mechanism.

BACKGROUND

Cancer of the skin is common worldwide. It is even the most common cancer in Australia and New Zealand. Non-melanoma cancer of skin represents in 2020, approximately 1.2 million new cancer (6.2% of total new cancer world-wide) and 63 thousand cancer death (0.6% of all cancer death). On the other hand, melanoma represents 324 thousand new cancer and almost the same amount of death: 57 thousand cancer death (0.6% of all cancer death). Prevention with sunscreen, and early detection for better treatment are key in order to reduce mortality.

Thus, a need still remains for a compute system with an explainable AI for skin lesions analysis mechanism to provide an objective analysis of skin abnormalities and cancer detection at an earlier stage of development. In view of the ever-increasing commercial competitive pressures, along with growing healthcare needs, healthcare expectations, and the diminishing opportunities for meaningful product differentiation in the marketplace, it is increasingly critical that answers be found to these problems. Additionally, the need to reduce costs, improve efficiencies and performance, and meet competitive pressures adds an even greater urgency to the critical necessity for finding answers to these problems.

Solutions to these problems have been long sought but prior developments have not taught or suggested any solutions and, thus, solutions to these problems have long eluded those skilled in the art.

DISCLOSURE OF THE INVENTION

An embodiment of the present invention provides a method of operation of a compute system including: segmenting a skin lesion in a patient image; constructing a normalized image by cropping the patient image and adding padding to position the skin lesion at a center of the normalized image; identifying a skin lesion classification, a skin lesion sub-class, and a risk level assessment by analyzing a symmetry axis, a border, color variation, and dermoscopic structures; and generating a skin lesion display including the normalized image, the skin lesion classification, the skin lesion sub-class, and the risk level assessment for displaying on a device.

An embodiment of the present invention provides a compute system, including a control circuit, including a processor, configured to: segment a skin lesion in a patient image; construct a normalized image by cropping the patient image and adding padding to position the skin lesion at the center of the normalized image; identify a skin lesion classification, a skin lesion sub-class, and a risk level assessment by analysis of a symmetry axis, a border, color variation, and dermoscopic structures; and generate a skin lesion display including the normalized image, the skin lesion classification, the skin lesion sub-class, and the risk level assessment for displaying on a device.

An embodiment of the present invention provides a non-transitory computer readable medium including instructions for a compute system, including: segmenting a skin lesion in a patient image; constructing a normalized image by cropping the patient image and adding padding to position the skin lesion at a center of the normalized image; identifying a skin lesion classification, a skin lesion sub-class, and a risk level assessment by analyzing a symmetry axis, a border, color variation, and dermoscopic structures; and generating a skin lesion display including the normalized image, the skin lesion classification, the skin lesion sub-class, and the risk level assessment for displaying on a device.

Certain embodiments of the invention have other steps or elements in addition to or in place of those mentioned above. The steps or elements will become apparent to those skilled in the art from a reading of the following detailed description when taken with reference to the accompanying drawings.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 15 are examples of a skin lesion display for analysis of an alternate form of cell carcinoma as identified by the XAI module in an embodiment.

FIG. 16 is an example of a skin lesion display for analysis of a Melanoma cancer as performed by in explainable AI (XAI) module an embodiment.

FIG. 21 is an example of a skin lesion display of one half of the skin cancer collision of FIG. 15.

FIG. 22 is an example of an analysis of a second half of the skin cancer collision of FIG. 15.

BEST MODE FOR CARRYING OUT THE INVENTION

Figure 1:
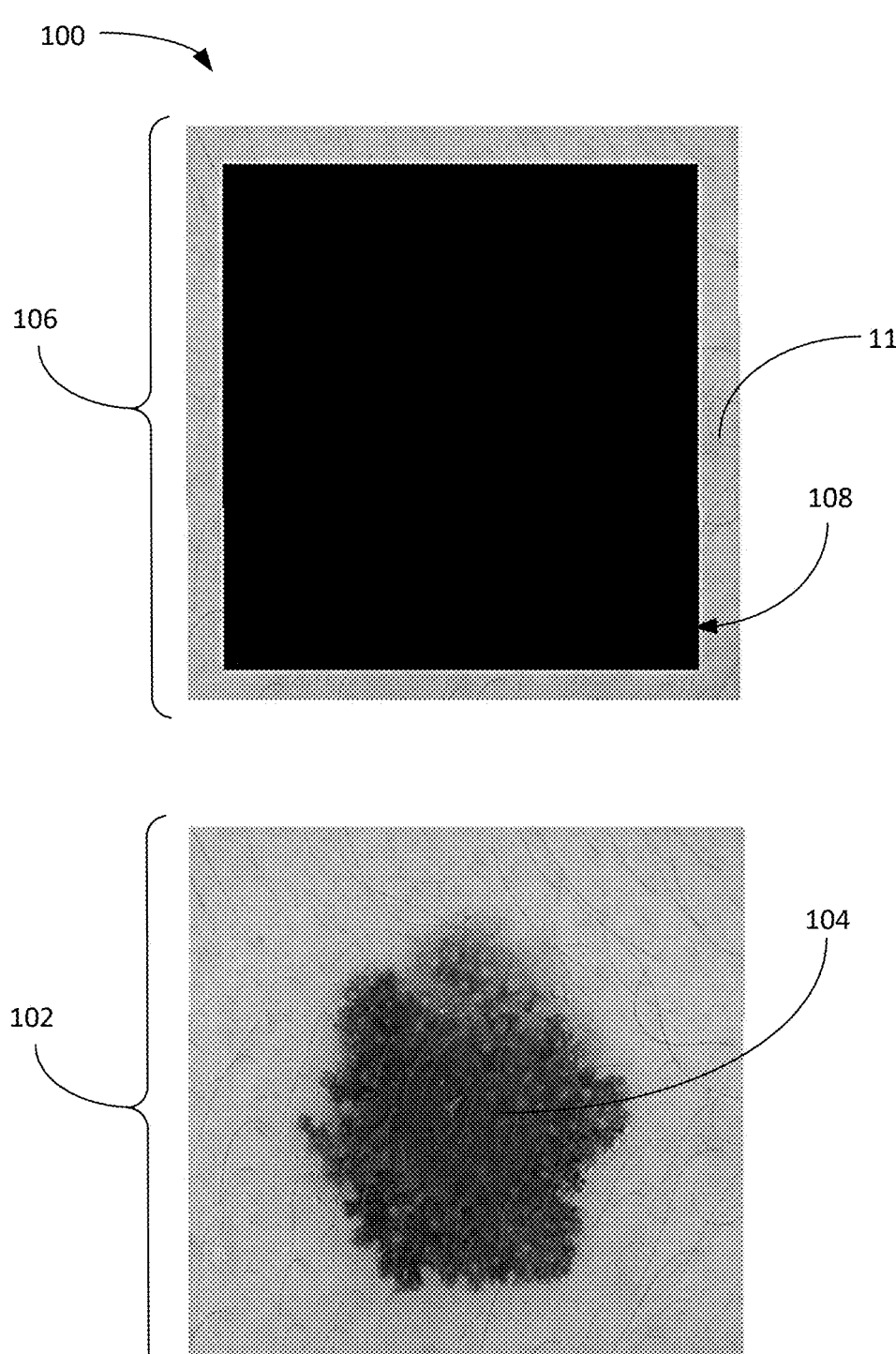
FIG. 1 is an example of a box mask application by an Explainable AI (XAI).

Deep Learning has been successful at detecting skin cancer from a lesion image, but its practical adoption is limited by the lack of explanation behind its decisions. The analysis of the lesion image based on two dermatology rules for lesion diagnosis is consistent with dermatology processes. First, a visualization tool can give practitioners additional context to how the model's decision has been reached. Second, a model variant, based on medical concepts, that is competitive with the baseline model while being more interpretable by the practitioner.

Embodiments can detect not only 10 different classes of skin cancer including Melanoma (MEL), Basal Cell Carcinoma (BCC), Epidermal tumors (EPI), Malignant lesions (MALO), Melanocytic Nevus (NV), Dermatofibroma (DF), Benign Adnexal Lesions (BAL), Benign Keratinocytic Lesions (BKL), Benign Vascular lesions (VASC) and Benign Lesions (BENO) but also 122 other subtypes for example Melanoma in situ, Melanoma nodular, etc. Example of embodiments use hierarchical learning (class and sub-class) which gives more accurate result then training with class information only. As an example, embodiments can include two steps: lesion segmentation and lesion classification. With this type of learning, each lesion has two labels, one for class and the other for sub-class or sub-type. If a lesion does not have sub-type information, the gradient will be set to zero so that it will not affect the back-propagation process. Embodiments underwent a blind test using a test set of 4926 images and resulting in an average of 0.95 of AUC (area under the curve) and 0.94 for MEL, 0.97 for NV, and 0.98 for BCC.

Skin cancers, including melanoma, are one of the most common cancers in the world. Early diagnosis is crucial to reduce morbidity and mortality. Human diagnosis by practitioners is based primarily on visual inspection, often with a dermatoscope for more details and comprehensive rules understood by the practitioner. The Asymmetrical, Border, Color, Diameter (ABCD) rule and the 7-point checklist (7PCL) are the most common rules applied by practitioners. The ABCD rule provides a decision based on asymmetry, border irregularity, color variation, and dermoscopic structure of the lesion, while the 7-point checklist (7PCL) provides a score based on 7 visual signs to detect suspicious lesions.

Embodiments continue to advance Deep Learning applied to skin lesion classification, as neural networks outperform dermatologists. A convolutional neural network (CNN)-based tool to assist dermatologists can enhance the detection and treatment of skin diseases. Embodiments of the model provide interpretability and the ability to provide an explanation to dermatologists to assist their decision. This limits the trust practitioners have in Artificial Intelligence (AI) and thus its adoption. Moreover, training data themselves contain biases non-meaningful for humans but are exploited by classification models. Understanding and quantifying how much of the decision aligns with medical concepts versus biases indicates the model's robustness. An embodiment provides insights into the neural network's behavior and provide meaningful explanations to practitioners.

Introduction of the neural net for skin lesion classification, can illustrate biases in the dataset that can be addressed by an Explainable AI (XAI), which can include:

1. Non-neural network algorithms can be developed to assess the criteria of the ABCD rule as a tool for practitioners.
2. The medical concepts learned by the model are analyzed using the seven-point checklist (7PCL)
3. Transfer of the model to a concept-based model to explain its decision based on medical signs that can be understood by the practitioners.

The Explainable AI (XAI) model can be a concept-based model based on an efficientnet-b4 pre-trained on ImageNet to extract embeddings and one classification head (2 linear layers with final Sigmoid activation) to predict the skin cancer class. A focal loss is used to train the model in order to eliminate class bias in the training data. The model predicts 10 classes, but can focus the explanations on benign vs malignant classes.

The following embodiments are described in sufficient detail to enable those skilled in the art to make and use the invention. It is to be understood that other embodiments would be evident based on the present disclosure, and that system, process, or mechanical changes may be made without departing from the scope of an embodiment of the present invention.

In the following description, numerous specific details are given to provide a thorough understanding of the invention. However, it will be apparent that the invention may be practiced without these specific details. In order to avoid obscuring an embodiment of the present invention, some well-known circuits, system configurations, and process steps are not disclosed in detail.

The drawings showing embodiments of the system are semi-diagrammatic, and not to scale and, particularly, some of the dimensions are for the clarity of presentation and are shown exaggerated in the drawing figures. Similarly, although the views in the drawings for ease of description generally show similar orientations, this depiction in the figures is arbitrary for the most part. Generally, the invention can be operated in any orientation. The embodiments of various components as a matter of descriptive convenience and are not intended to have any other significance or provide limitations for an embodiment of the present invention.

The term "module" or "unit" or "circuit" referred to herein can include or be implemented as or include software running on specialized hardware, hardware, or a combination thereof in the present invention in accordance with the context in which the term is used. For example, the software can be machine code, firmware, embedded code, and application software. The software can also include a function, a call to a function, a code block, or a combination thereof.

Also, for example, the hardware can be gates, circuitry, processor, computer, integrated circuit, integrated circuit cores, memory devices, a pressure sensor, an inertial sensor, a microelectromechanical system (MEMS), passive devices, physical non-transitory memory medium including instructions for performing the software function, a portion therein, or a combination thereof to control one or more of the hardware units or circuits. Further, if a "module" or "unit" or a "circuit" is written in the claims section below, the "unit" or the "circuit" is deemed to include hardware circuitry for the purposes and the scope of the claims.

The module, units, or circuits in the following description of the embodiments can be coupled or attached to one another as described or as shown. The coupling or attachment can be direct or indirect without or with intervening items between coupled or attached modules or units or circuits. The coupling or attachment can be by physical contact or by communication between modules or units or circuits, such as wireless communication.

The word "module" or "model" can be also be used interchangeable depending on the context it is described or used in the written description. The "model" can represent one or more artificial intelligence models, machine learning models, or a combination thereof.

It is also understood that the nouns or elements in the embodiments can be described as a singular instance. It is understood that the usage of singular is not limited to singular but the singular usage can be applicable to multiple instances for any particular noun or element in the application. The numerous instances can be the same or similar or can be different.

Referring now to FIG. 1, therein is shown an example of a box mask application 100 by an Explainable AI (XAI). The example of a box mask application 100 depicts a dermoscopic image 102 including a skin lesion 104, an example of the skin lesion is skin cancer. In order to prevent an interpretation bias, A masked image 106 can be created by applying a box mask 108 to completely cover the skin lesion 104 and leave a border region 110 exposed for analysis during a training process.

Training uses an internal dataset of 104,000 images. Inspired by a previous approach revealing biases in the ISIC dataset. The focal loss can determine how biased is the training dataset. Indeed, the presence of biases creates spurious correlations that the model may exploit instead of meaningful information, leading to a seemingly better accuracy but lower robustness. A proposed update to the methodology by training and testing an XAI model on the masked image 106 where the box mask 108 covering 70% of pixels is applied, hiding the entirety of the skin lesion 104, as illustrated in FIG. 1.

When comparing the baseline model with the XAI model trained with the box mask 104, classification performances drop, but they are far from random, i.e., predicting class based on frequency in the train set. The Area Under the Receiving Operating Characteristic (AUROC) is even similar to the performances of dermatologists. Since the XAI model can make better than random classification when the skin lesion 104 is masked, the existence of spurious correlations within the dataset can be confirmed. This confirms the importance of knowing which information the XAI model uses, as we investigate in the following sections.

TABLE 1

| Classification metrics on internal test set. | | | | |
| --- | --- | --- | --- | --- |
| | Baseline | Box Model | Random | Doctors |
| Accuracy | 73% | 35% | 17.8% | — |
| AUROC | 0.92 | 0.68 | — | 0.67 |

Since the Doctor's AUROC sets the current standard for analysis of the skin lesion 104, the performance of the XAI model provides a comparable result. The next step will be to analyze what criteria enhances the accuracy of the XAI model.

Figure 2:
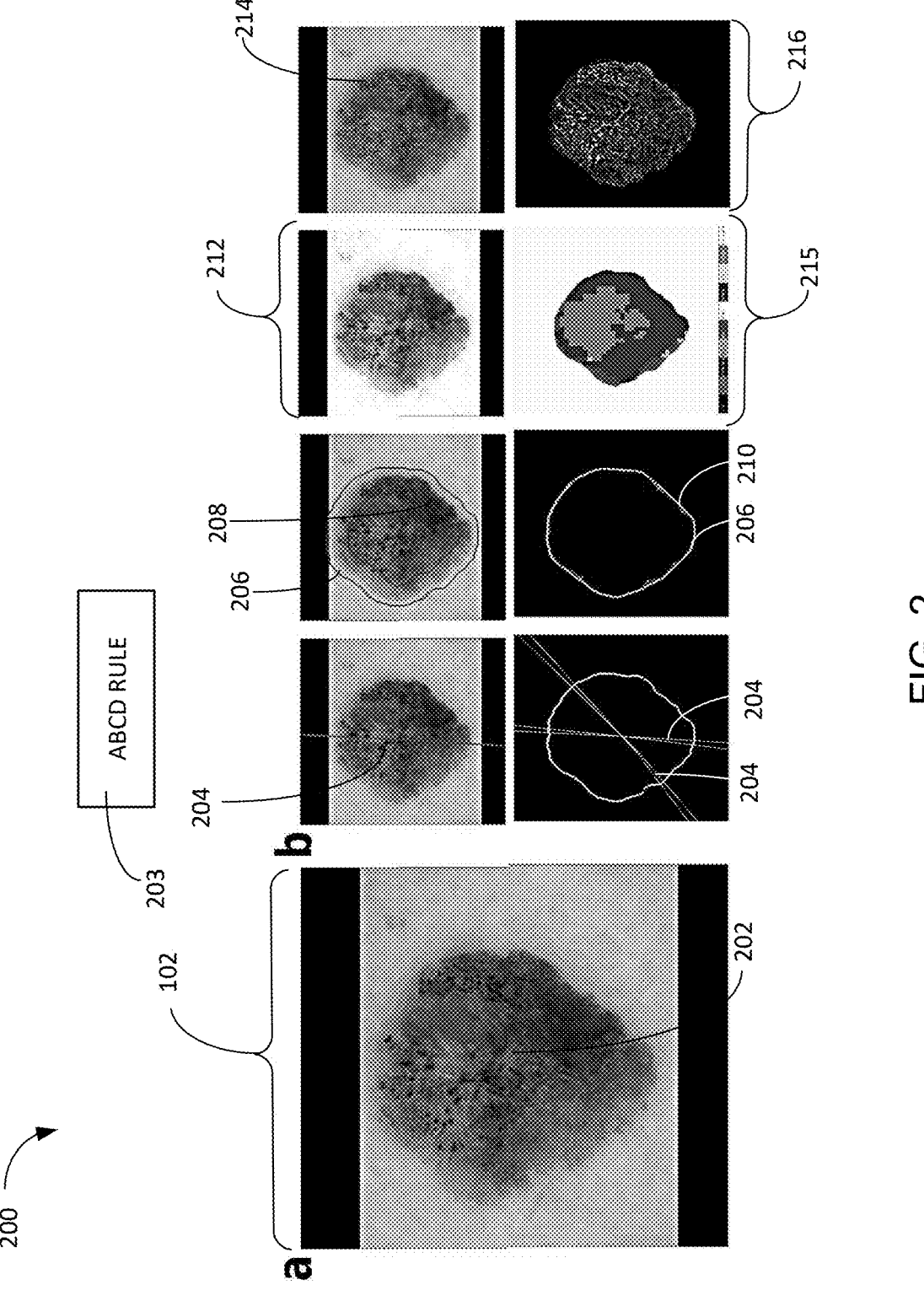
FIG. 2 is an example of the Explainable AI (XAI) model applying an ABCD rule for processing a pigmented lesion.

Referring now to FIG. 2, therein is shown an example of the Explainable AI (XAI) model 200 applying an ABCD rule 203 for processing a pigmented lesion 202. The example of the ABCD rule 203 processing the pigmented lesion 202 depicted in the dermoscopic image 102.

The ABCD rule is a simple yet effective tool for dermatologists to assess the pigmented lesion 202 for potential malignancy. Here, we apply each ABCD rule 203 as an image processing technique to analyze the dermoscopic image 102. The ABCD rule 203 can be leveraged to provide additional visual information to clinicians. The XAI model 200 can additionally derive metrics from the ABCD rule 203 to study their correlation with our dataset's ground truth.

Asymmetry, Irregular shapes, and uneven color distribution are strong indications of melanoma. The Explainable AI (XAI) model 200 can quantify asymmetry by first isolating the pigmented lesion 202 using segmentation. Then, the XAI model 200 can identify potential symmetry axes 204 based on the segmented region's shape. These potential symmetry axes 204 are informed by the prior shape asymmetry analysis, ensuring color assessment aligns with potential shape irregularities. If there is no symmetry in the shape, there will be no symmetry in colors. The XAI model 200 calculates the Intersection over Union (IoU) between the pigmented lesion 202 and its mirrored counterpart for each of the potential symmetry axes 204, considering both shape and color distribution weighted by color presence. A significant deviation from an IoU of 1 (indicating perfect overlap) suggests asymmetry, potentially signifying melanoma.

Borders 206 that are smooth are characteristic of benign lesions. Conversely, melanomas often exhibit notched, sharp, or uneven borders 206. We assess regularity of the border 206 using the convex hull method. By comparing a convex hull 208 representing the smallest convex shape encompassing the entirety of the pigmented lesion 202, we highlight 210 the discrepancy between the border 206 and the convex hull 208. The highlight 210 represents the number of deviations indicating its irregularity and its potential malignancy.

To analyze color variation 212, melanomas often exhibit a mix of brown, black, blue, white, and red hues compared to uniformly brown benign nevi an image normalization 214 is performed. The color variation 212 of the pigmented lesion 202 can define dermoscopic structures 215. The dermoscopic structures 215 can define areas of the pigmented lesion 202 that represent different surface contours, color densities, textures, and shapes. This ensures a consistent color basis for assessment across the pigmented lesion 202, addressing illumination variations. Image normalization 214 involves converting the pigmented lesion 202 to a negative grayscale format 216, identifying the highest and background intensities ($I_{top}$ and $I_{background}$), and replacing pixel intensities based on Equation 1, where $I_{range}=I_{top}-I_{background}$, $I_0$ represents the original intensity, and I represents the new intensity:

$$I = \frac{\min(I\text{range}, \max(I0 - I\text{background}, 0)}{I\text{range}} \quad \text{(EQ 1)}$$

This results in the negative grayscale format 216 suitable for further analysis. The segmentation the pigmented lesion 202 into smaller regions and computation of the most frequent color in each, based on a dermatologist-defined list, provides greater clarity to the color variation in the pigmented lesion 202 to determine the dermoscopic structures 215. When visualizing features and patterns within the pigmented lesion 202 through dermoscopy, dermatologists refer to the dermoscopic structures, or differential structures, such as the pigment network and vascular patterns as indicators of malignancy. Atypical features like bluewhite veil or irregular pigmentation are strongly associated with melanoma.

Figure 3:
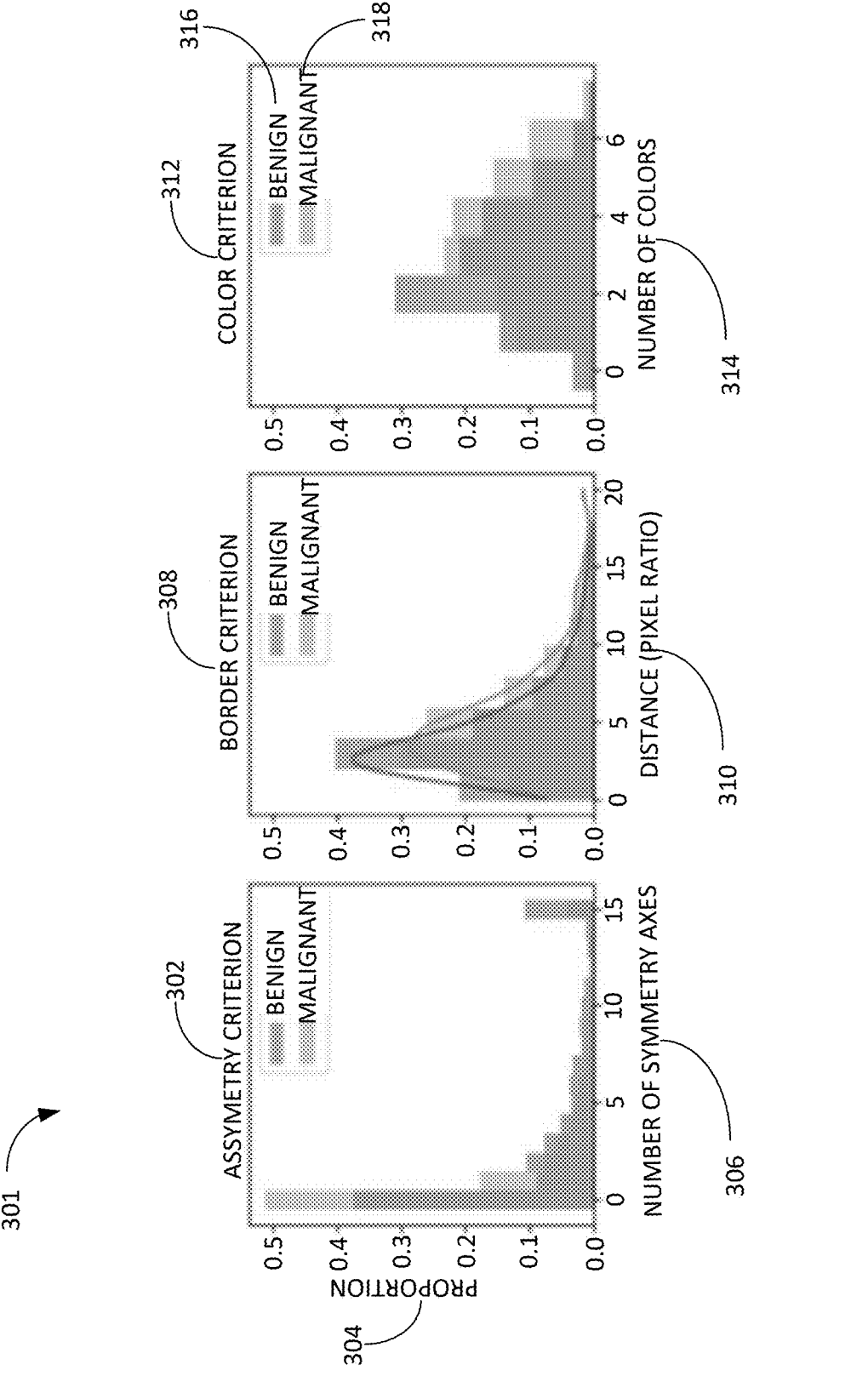
FIG. 3 is an exemplary graphical comparison between malignant and benign skin lesions based on Asymmetry, Irregularity, and Colorization.

Referring now to FIG. 3, therein is shown an exemplary graphical comparison 301 between malignant and benign skin lesions based on Asymmetry, Irregularity, and Colorization. The exemplary graphical comparison 301 depicts an asymmetry criterion 302, a border criterion 308, and a color criterion 312.

Applying the ABCD rule 203 of FIG. 2 on the dermoscopic image 102 of FIG. 1 featuring a melanoma requires the following steps. The dermoscopic image 102 is padded to a square format. Then the asymmetry, border, color, and dermoscopic structure criteria is applied to the dermoscopic image 102. The XAI model 200 of FIG. 2 determines the best symmetry axes 204 of FIG. 2 found based on shape and color, the border 206 of FIG. 2 of the pigmented lesion 202 of FIG. 2 is displayed in green with its inner and outer border 206 in red, the normalized image 216, the highlighted in green dermoscopic structure. The XAI model 200 identifies all the symmetry axes 204 found with an IoU of at least 0.9, the convex hull 210 based on the detected border 206 of the pigmented lesion 202 in yellow, the detected border 206 of the pigmented lesion 202 in red, and the highlights 210 of FIG. 2 displayed as pink dots, the color variations inside the pigmented lesion 202, the enhanced result of a Meijering filter of the normalized image 216 of FIG. 2. The asymmetry criterion 302 compares a proportion 304 of the pigmented lesion 202 to a number of symmetry axes 306. The graph indicates that as the number of symmetry axes 306 increases, the higher probability that the pigmented lesion 202 is benign 316. When the number of symmetry axes 306 is zero, the higher probability that the pigmented lesion 202 is malignant 318.

The border criterion 308 compares the proportion 304 of the pigmented lesion 202 to a distance 310 that is measured as a pixel ratio of the border 206 of the pigmented lesion 202. The border criterion 308 does not represent a clear distinction between benign 316 and malignant 318, except for the very lowest distances, where benign 316 overrides the graph. The border criterion 308 indicates that the distance 310 of five and up has a slightly higher probability of being malignant 318.

The color criterion 312 compares the proportion 304 of the pigmented lesion 202 to a number of colors 314 found in the pigmented lesion 202. The graph indicates that two or fewer of the number of colors 314 has a higher probability of being benign 316, but three or more as the number of colors 314 has a higher probability of being malignant 318. It is understood that the higher the number of colors 314 does not mean that the pigmented lesion 202 must be malignant 318, but it is a strong indicator.

Figure 4:
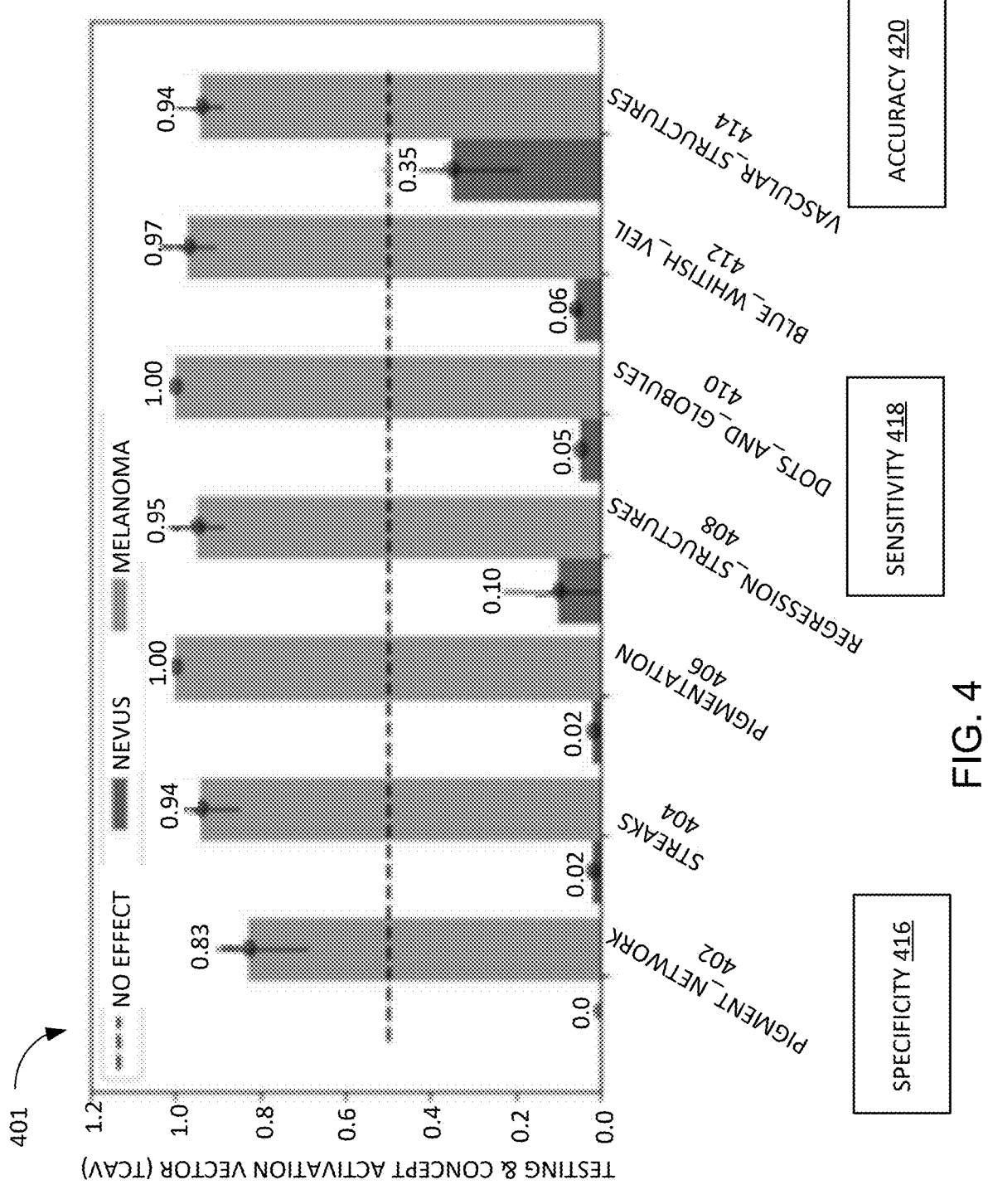
FIG. 4 is an exemplary bar graph comparison of 7PCL medical elements.

Referring now to FIG. 4, therein is shown an exemplary bar graph comparison of medical elements 401, such as seven point check list (7PCL) medical elements. The Testing with Concept Activation Vector (TCAV) approach on the 7PCL, mean and standard deviation on 10 runs of the XAI model 200 of FIG. 2. The medical elements 401 of the seven point check list (7PCL) are pigment network 402, streaks 404, pigmentation 406, regression structures 408, dots and globules 410, blue whitish veil 412, vascular structures 414, or a combination thereof.

Further analysis of the concepts learned by the XAI model using medical annotations. The Interactive Atlas of Dermoscopy contains about 1,000 images with diagnosis and a label for each sign of the 7PCL. These signs indicate a suspicious lesion.

The signs are used as the medical elements 401 and test whether the XAI model 200 uses them with the TCAV approach. First two banks of the dermoscopic images 102 of FIG. 1 are created for each sign of a suspicious lesion: one bank containing the sign and one without it (i.e., sign labeled as "absent" or "regular" or "typical"). A linear classifier was fit to separate the embeddings into two classes. A concept is the vector normal to the decision boundary. Then test if this concept is important for a class (nevus or melanoma) using a third bank of the dermoscopic images 102 of the class, with no overlap with the other two banks. For each image, the derivative of the class logit with regard to the embedding is computed. The TCAV score is the ratio of images whose derivative is in the same direction as the concept vector indicating a positive dot product. A score near 1 means the concept is important for the class, while a score around 0.5 corresponds to a random concept.

The TCAV method gives insight into the global model behavior but does not provide a precise explanation for a single image. An alternate model that predicts the 7 signs of 7PCL instead of predicting classes was attempted. The skin lesion 104 of FIG. 1 is detected as malignant 318 of FIG. 3 if it has a score higher than 3. The decision is then made based on detected signs: a major sign gives 2 points, while a minor sign gives 1 point, and the skin lesion 104 is suspected as malignant 318 if it has a score of 3 or more.

The loss rewards a correct classification of each sign individually and a correct diagnosis by comparing the true score to the score computed from predicted signs. The total loss is:

$$L(y, \hat{y}) = \sum_{k=1}^{7} CE(yi, \hat{y}i) + MSE\left(\sum_{k=1}^{7} \mathbb{1}(yi \neq 0), \sum_{k=1}^{7} \mathbb{1}(\hat{y}i \neq 0)\right) \quad \text{(EQ 2)}$$

where y and ŷ are the vectors of true and predicted signs, CE is cross-entropy, and MSE is mean squared error. Models are trained until the mean validation accuracy increases.

First analyze of the baseline model's decision a posteriori and then compare it to its more interpretable concept-based version.

In order to assess whether the criteria derived from the ABCD rule 203 of FIG. 2 can be used as an indicator for practitioners, a comparison to the baseline model's decision is run, along with the class prediction. Most criteria are visual, as illustrated in FIG. 2. Quantitative results are added by comparing 3 distributions for both malignant 318 of FIG. 3 and benign 316 of FIG. 3 classes: the number of symmetry axes 204 of FIG. 2, the highest distance 310 of FIG. 3 between the skin lesion's 104 actual border 206 of FIG. 2 and the convex hull 210 of FIG. 2, and the number of colors 314 of FIG. 3 in a single skin lesion 104. As shown in FIG. 3, a distribution shift is observed between benign 316 and malignant 318 lesions on the 3 criteria. As expected, malignant 318 lesions tend to have fewer symmetry axes 204, a border 206 further away from its convex hull 210, and contain a higher number of the number of colors 314.

A test of the importance of each sign of 7PCL for the classification with TCAV, and each sign corresponding to a concept. For each sign and each class, the concept is computed 10 times on random train/test splits of the dermoscopic images 102 with and without concept.

As displayed in FIG. 4, all signs of the 7PCL are important for classifying a melanoma, with scores >0.8. On the contrary, all signs but one disfavor the nevus class, the vascular structures 414 sign being close to a random concept.

First assess the interpretable model by its average binary accuracy on each sign (present/absent) and the mean absolute error (MAE) between the resulting score and true score. For reference, true scores range from 0 to 7. Table 2 displays that accuracy averaged over signs is better with CE only training, but the resulting score is further from the true score. The accuracy is surprisingly low: even if the concepts derived from these signs are important for the classification model, it cannot recognize their presence reliably. This could be due to the small size of the Atlas dataset. The 7PCL aims to detect malignant 318 lesions (melanoma or other). We define a binary classification task on the Atlas test set: to predict whether a lesion is malignant 318 or benign 316.

TABLE 2

| Test metrics on interpretable models | | |
| --- | --- | --- |
| Training | MSE + CE | CE-only |
| Mean Acc. | 69.6% | 73.6% |
| MAE | 1.50 | 1.71 |

In Table 3, a comparison between the baseline model and the XAI model 200 version. None of them has been explicitly trained on this task: the baseline predicts 10 different classes, while the interpretable model predicts 7 signs on which the 7PCL decision rule is applied. Interestingly, training the XAI model 200 under MSE+CE is beneficial in terms of diagnosis vs using CE only, even if individual sign prediction is lower. Moreover, the gap between the interpretable model and the baseline is only 2% accuracy.

TABLE 3

| Models comparison on binary classification | | | |
| --- | --- | --- | --- |
| Model | Baseline | XAI model | CE-only |
| 2-class acc. | 78.9% | 76.6% | 73.0% |

Therefore, the effort is based on two rules used by dermatologists: the ABCD rule 203 of FIG. 2 and the 7-point checklist. The derived criteria from the ABCD rule 203, both visual and numerical, using non-neural algorithms to provide additional information for the neural net classification. The XAI model 200 uses the medical concepts in the 7PCL, and a more interpretable model was derived predicting each of the seven signs. This model has a good trade-off between explainability and performance in the binary classification of malignant 318 lesions from benign 316 ones.

Embodiments can perform sub-class-based training technique for deep neural networks (DNN) that lead to an improvement in both robustness and accuracy. The criterion of the embodiment for identifying the neglected classes are input during the training. An embodiment also proposed to split the neglected classes into sub-classes using a clustering method and apply a new loss function using sub-class partitions. The embodiment resulted in a DNN with higher overall generalization performance on several benchmarks datasets for multiclass and multilabel classification. An embodiment has trained a model to split each class into estimated sub-classes via unsupervised clustering in the model's feature space. These estimated sub-class labels are then used during the training of the classification model. The resulting model is more robust and has a significantly higher worst-case sub-class accuracy on several real-world and benchmark image classification datasets including "ISIC challenge 2020".

Example of embodiments, can be referred to as Explainable AI, using hierarchical learning. Embodiments generate a very detailed classification system that contains 10 classes and 122 sub-classes, in which a class might have up to 16 sub-classes. Embodiments do not estimate the sub-class labels using clustering method, but rather set the gradient be zero so that missing sub-class will not affect the learning process.

Embodiments of the skin lesion classification system. Skin cancer detection itself is a very complex classification problem since there are thousands of lesion types which have been known. Besides, the famous mimickers, such as melanoma and nevus, make it extremely hard to distinguish between benign 316 and malignant 318 lesions. To tackle a such difficult classification problem, it is crucial to have a good classification system. Embodiments address some serious weakness of classification system. Embodiments addressed these weaknesses with a new classification system which is much more detailed with 10 classes and 122 sub-classes. Hereafter embodiments implement the discoveries into the classification system.

An ISIC classification system for skin cancer detection contains nine classes: melanoma (MEL), melanocytic nevus (NV), basal cell carcinoma (BCC), actinic keratosis (AK), benign keratosis including solar lentigo, seborrheic keratosis and lichen planus-like keratosis (BKL), dermatofibroma (DF), vascular lesion (VASC), squamous cell carcinoma (SCC), and unknown (UNK). This system covers the most common malignant 318 and benign 316 classes of the skin lesions 104. It is easy for doctors to annotate, and also more informative than the binary classification "malignant 318 vs benign 316". However, the ISIC classification system has some serious weaknesses that will be explain hereafter.

Firstly, the ISIC classification system is ambiguous and not backward-compatible. Many skin lesions are difficult to classify into one of the nine given classes properly. For example, clear cell acanthoma and porokeratosis are benign keratinocytic lesions, but they are not included in the BKL class by ISIC's definition. Another example is the Bowen disease lesion which was included in AKIEC, together with AK, in "ISIC challenge 2018". However, in "ISIC challenge 2019", Bowen disease lesion is included in SCC and not AK class.

Secondly, many uncommon but important types of skin lesions, both benign 316 and malignant 318, are missing in the classification. Examples include Merkel cell carcinoma, kaposi sarcoma, dermatofibrosarcoma protuberans, sebaceous gland hyperplasia, etc. These lesions all become unknown (UNK) in the ISIC classification system, and therefore, the trained model cannot recognize them in real life application.

Finally, the ISIC classification system does not provide enough information for determining the cancer risk level of skin lesions since lesions in the same class may have very different cancer risk levels. For example, pyogenic granuloma and cherry angioma are both in VASC class. However, pyogenic granuloma must have much higher cancer risk level because it looks very similar to other malignant 318 lesions such as amelanotic melanoma and kaposi sarcoma. Similarly, Spitz nevus and dysplastic nevus look very similar to melanoma hence they must have much higher cancer risk level compared with other benign nevi.

A comparison setting participant: 3 doctors (Labeille, Chloé, Ravni) vs AI (Explainable AI eta version) total 972 images of 243 unique lesions taken from 4 dermoscopes: FotoFinder, Visiomed, HorusX30, HorusX20. Doctor's answer Hypothesis/Dx: 'AK', 'BCC', 'Cyst', 'Lentigo', 'MEL', 'MEL_LM', 'MEL_Meta', 'NV', 'NV_Atyp', 'NV_Spitz', 'PAGET', 'SCC', 'SK', dunno Nature: can be defined as malignant 318, benign 316, or dunno Treatment/Modality: can be selected from return to GP (return), monitor 3 months (M3), biopsy, excision, or a combination thereof.

Here is the summary of 972 images by type and nature.

| Type | Images | Lesions | #Benign 316 | #Malignant 318 |
|---|---|---|---|---|
| AK | 16 | 4 | 16 | 0 |
| BCC | 252 | 63 | 0 | 252 |
| Cyst | 8 | 2 | 8 | 0 |
| Lentigo | 24 | 6 | 24 | 0 |
| MEL | 272 | 68 | 0 | 272 |
| MEL_LM | 76 | 19 | 0 | 76 |
| MEL_Meta | 12 | 3 | 0 | 12 |
| NV | 196 | 49 | 196 | 0 |
| NV_Atyp | 32 | 8 | 32 | 0 |
| NV_Spitz | 8 | 2 | 8 | 0 |
| Paget | 4 | 1 | 0 | 4 |
| SCC | 40 | 10 | 0 | 40 |
| SK | 32 | 8 | 32 | 0 |
| Sum | 972 | 243 | 316 | 656 |

Statistical Study Objectives

Principal objective: reproducibility of the dermatologist's diagnosis.

Secondary Objectives:

Reproducibility of AI's diagnosis.

Accuracy 420 of dermatologists and AI on nature (benign 316/malignant 318) of the skin lesions 104, and diagnosis hypothesis, according to separate utilization or combined utilization of dermatoscope.

Improvement of accuracy 420 when combined versus separate utilization of dermatoscopes.

Kappa Interpretation:

| Kappa | Interpretation |
|---|---|
| <0 | No agreement |
| 0.0-0.20 | Slight agreement |
| 0.21-0.40 | Fair agreement |
| 0.41-0.60 | Moderate agreement |
| 0.61-0.80 | Substantial agreement |
| 0.81-1.00 | Almost perfect agreement |

Agreement in diagnosis hypothesis kappa is computed under assumption that $$NV = NV\_Atyp = NV\_Spitz$$

$$MEL = MEL\_LM = MEL\_Meta$$

95% confidence level (CI) is computed using bootstrap sampling with 1000 repetitions. The following table indicates the relative capabilities of three clinicians versus the XAI model 200 of FIG. 2 with input from various medical image capture devices.

| | kappa | Dr. Labeille | Dr. Chloé | Dr. Ravni | XAI |
|---|---|---|---|---|---|
| Cohen's kappa | FF vs Visiomed | 0.404-0.556 | 0.407-0.549 | 0.406-0.566 | 0.749-0.869 |
| | FF vs HorusX30 | 0.373-0.523 | 0.336-0.476 | 0.305-0.469 | 0.684-0.816 |
| | FF vs HorusX20 | 0.368-0.525 | 0.337-0.471 | 0.321-0.486 | 0.656-0.792 |
| | Visiomed vs HorusX30 | 0.387-0.541 | 0.359-0.506 | 0.334-0.505 | 0.629-0.771 |
| | Visiomed vs HorusX20 | 0.435-0.590 | 0.403-0.546 | 0.360-0.536 | 0.650-0.785 |
| | HorusX30 vs HorusX20 | 0.450-0.605 | 0.405-0.548 | 0.369-0.545 | 0.710-0.836 |
| Fleiss' kappa | Global | 0.426-0.527 | 0.395-0.493 | 0.372-0.487 | 0.696-0.796 |

Remarks dermatologists have moderate agreement when using different dermoscopes while XAI has substantial agreement.

95% CI of XAI is separated from that of dermatologists=>XAI's kappa coefficient is statistically higher than that of dermatologists huge overlap of 95% CI between dermatologists=>difference in kappa coefficient of dermatologists is not statistically significant

Agreement in Nature of Lesion

| | kappa | Labeille | Chloé | Ravni | XAI |
|---|---|---|---|---|---|
| Cohen's kappa | FF vs Visiomed | 0.41 | 0.39 | 0.4 | 0.58 |
| | FF vs HorusX30 | 0.39 | 0.43 | 0.33 | 0.54 |
| | FF vs HorusX20 | 0.47 | 0.42 | 0.3 | 0.56 |
| | Visiomed vs HorusX30 | 0.39 | 0.48 | 0.39 | 0.45 |
| | Visiomed vs HorusX20 | 0.46 | 0.52 | 0.36 | 0.47 |
| | HorusX30 vs HorusX20 | 0.48 | 0.44 | 0.42 | 0.53 |
| Fleiss' kappa | Global | 0.43 | 0.44 | 0.36 | 0.52 |

| | kappa 95% CI | Labeille | Chloé | Ravni | XAI |
|---|---|---|---|---|---|
| Cohen's kappa | FF vs Visiomed | 0.320-0.504 | 0.300-0.480 | 0.293-0.511 | 0.480-0.660 |
| | FF vs HorusX30 | 0.282-0.490 | 0.339-0.513 | 0.232-0.433 | 0.445-0.631 |
| | FF vs HorusX20 | 0.368-0.567 | 0.333-0.509 | 0.190-0.394 | 0.462-0.647 |
| | Visiomed vs HorusX30 | 0.277-0.495 | 0.378-0.578 | 0.287-0.501 | 0.350-0.545 |
| | Visiomed vs HorusX20 | 0.351-0.568 | 0.430-0.597 | 0.239-0.476 | 0.374-0.559 |
| | HorusX30 vs HorusX20 | 0.372-0.574 | 0.345-0.528 | 0.298-0.533 | 0.441-0.621 |
| Fleiss' kappa | Global | 0.357-0.493 | 0.378-0.501 | 0.291-0.435 | 0.458-0.583 |

Remarks

XAI, Labeille, Chloé has moderate agreement while Ravni has fair agreement

CI of XAI is separated from CI of Ravni=>difference in kappa of XAI & Ravni is statistically significant.

huge overlap between CI of Labeille & Chloé=>difference in kappa of Labeille & Chloé is not statistically significant

Agreement in Treatment Modality

| | kappa | Labeille | Chloé | Ravni | XAI |
|---|---|---|---|---|---|
| Cohen's kappa | FF vs Visiomed | 0.49 | 0.42 | 0.33 | 0.52 |
| | FF vs HorusX30 | 0.36 | 0.37 | 0.27 | 0.44 |
| | FF vs HorusX20 | 0.41 | 0.46 | 0.25 | 0.51 |
| | Visiomed vs HorusX30 | 0.35 | 0.4 | 0.27 | 0.4 |
| | Visiomed vs HorusX20 | 0.57 | 0.43 | 0.32 | 0.45 |
| | HorusX30 vs HorusX20 | 0.46 | 0.57 | 0.37 | 0.46 |
| Fleiss' kappa | Global | 0.43 | 0.44 | 0.3 | 0.46 |

| | kappa 95% CI | Labeille | Chloé | Ravni | XAI |
|---|---|---|---|---|---|
| Cohen's kappa | FF vs Visiomed | 0.381-0.591 | 0.336-0.500 | 0.241-0.434 | 0.435-0.601 |
| | FF vs HorusX30 | 0.256-0.471 | 0.282-0.451 | 0.174-0.363 | 0.361-0.527 |

| | kappa 95% CI | Labeille | Chloé | Ravni | XAI |
|---|---|---|---|---|---|
| | FF vs HorusX20 | 0.304-0.526 | 0.372-0.533 | 0.165-0.342 | 0.414-0.594 |
| | Visiomed vs HorusX30 | 0.246-0.451 | 0.315-0.490 | 0.176-0.369 | 0.306-0.491 |
| | Visiomed vs HorusX20 | 0.449-0.681 | 0.342-0.513 | 0.208-0.427 | 0.356-0.532 |
| | HorusX30 vs HorusX20 | 0.350-0.559 | 0.485-0.639 | 0.268-0.466 | 0.372-0.549 |
| Fleiss' kappa | Global | 0.343-0.513 | 0.383-0.491 | 0.247-0.355 | 0.405-0.520 |

Accuracy 420 of Diagnosis Hypothesis for Separated and Combined Use of Dermoscope $$\text{Accuracy } 420 = (\text{\# correct } dx \text{ hypothesis})/(\text{\# image})$$

image=972 when consider all images image=243 when consider each dermoscope or combined use of dermoscope image=#image of the disease when consider only one disease correct dx hypothesis is computed under the assumption that

*i.*   $NV = NV\_Atyp = NV\_Spitz$

*ii.*   $MEL = MEL\_LM = MEL\_Meta$

95% CI is computed using bootstrap sampling with 1000 repetitions

Accuracy 420 on all Images and for Each Disease

| disease | Labeille | Chloé | Ravni | XAI |
|---|---|---|---|---|
| AK | 0 | 0.56 | 0.25 | 0.75 |
| BCC | 0.62 | 0.5 | 0.41 | 0.94 |
| Cyst | 0 | 0.13 | 0 | 0.75 |
| Lentigo | 0.21 | 0.13 | 0.04 | 0.13 |
| MEL | 0.82 | 0.68 | 0.9 | 0.77 |
| NV | 0.42 | 0.68 | 0.45 | 0.77 |
| PAGET | 0 | 0 | 0.25 | 0 |
| SCC | 0 | 0.43 | 0.4 | 0.4 |
| SK | 0.13 | 0.28 | 0.06 | 0.69 |
| all images | 0.58 | 0.59 | 0.57 | 0.77 |
| all images 95% CI | 0.545-0.607 | 0.557-0.616 | 0.542-0.606 | 0.747-0.800 |

Remarks

Ravni has highest accuracy 420 on MEL

XAI has highest accuracy 420 on AK, BCC, Cyst, NV, SK

Accuracy 420 on all images of XAI is higher than that of dermatologists and this difference is statistically significant.

There is a slight difference in accuracy 420 on all images of the dermatologists, but this difference is not statistically significant.

Accuracy 420 on Separated & Combined Use of Dermo-scopes

Dx hyp for combined use of dermoscopes is defined as follows:

if 4 answers are all dunno, the final answer is dunno.

if 4 answers contain only one disease & the rest is dunno, the final answer is that disease.

if 4 answers contain more than one diseases and there is only one disease X with highest frequency, the final answer is X.

if 4 answers contain more than one disease and there is more than one diseases with highest frequency, the final answer is dunno.

| | Accuracy 420 | | | | accuracy 95% CI | | | |
|---|---|---|---|---|---|---|---|---|
| | Labeille | Chloé | Ravni | XAI | Labeille | Chloé | Ravni | XAI |
| FotoFinder | 0.56 | 0.57 | 0.58 | 0.78 | 0.506-0.626 | 0.514-0.630 | 0.510-0.642 | 0.728-0.831 |
| Visiomed | 0.67 | 0.65 | 0.64 | 0.74 | 0.613-0.733 | 0.593-0.708 | 0.584-0.704 | 0.687-0.794 |
| HorusX30 | 0.49 | 0.5 | 0.5 | 0.73 | 0.428-0.551 | 0.440-0.568 | 0.444-0.564 | 0.675-0.786 |
| HorusX20 | 0.52 | 0.56 | 0.53 | 0.74 | 0.457-0.580 | 0.498-0.626 | 0.465-0.584 | 0.683-0.794 |
| combined dermoscope | 0.67 | 0.58 | 0.56 | 0.73 | 0.613-0.728 | 0.514-0.642 | 0.502-0.621 | 0.671-0.782 |

Remarks

Among 4 dermoscopes, dermatologists have higher accuracy 420 on Visiomed while XAI has the highest accuracy 420 on FotoFinder.

combined use of dermoscopes does not improve accuracy 420.

p value is computed by two-tailed z-test, using statsmodels.stats.proportion.proportions_ztest

| p value | Labeille | Chloé | Ravni | XAI |
|---|---|---|---|---|
| FF vs Visiomed | 0.015 | 0.078 | 0.164 | 0.29 |
| FF vs HX30 | 0.123 | 0.122 | 0.084 | 0.207 |
| FF vs HX20 | 0.363 | 0.855 | 0.274 | 0.29 |
| FF vs combined | 0.015 | 0.855 | 0.714 | 0.207 |
| Visiomed vs HX30 | 0.0 | 0.001 | 0.002 | 0.838 |
| Visiomed vs HX20 | 0.001 | 0.052 | 0.013 | 1.0 |
| Visiomed vs combined | 1.0 | 0.114 | 0.079 | 0.838 |
| HX30 vs HX20 | 0.525 | 0.173 | 0.525 | 0.838 |
| HX30 vs combined | 0.0 | 0.084 | 0.173 | 1.0 |
| HX20 vs combined | 0.001 | 0.714 | 0.466 | 0.838 |

Accuracy 420 of Nature for Separated and Combined Use of Dermoscope.

$$\text{Sensitivity} = (\# \text{ correct malignant } dx)/(\# \text{ malignant images})$$

where #malignant images=656

$$\text{Specificity} = (\# \text{ correct benign } dx)/(\# \text{ benign images})$$

where #benign images=316

$$\text{Accuracy } 420 = (\text{\# correct nature } dx)/(\text{\# images})$$

images=972 if consider all images #images=243 if consider separated or combined use of dermoscope
95% CI is computed using bootstrap sampling with 1000 repetitions
Sensitivity, Specificity, Accuracy on all Images

|  | Labeille | Chloé | Ravni | XAI |
|---|---|---|---|---|
| Specificity 416 | 0.17 | 0.52 | 0.34 | 0.56 |
| Sensitivity 418 | 0.78 | 0.54 | 0.86 | 0.82 |
| Accuracy 420 | 0.58 | 0.53 | 0.69 | 0.74 |
| accuracy 95% CI | 0.551-0.612 | 0.502-0.567 | 0.663-0.718 | 0.713-0.766 |

Remarks

Ravni has highest sensitivity 418 while XAI has highest specificity 416.
XAI has highest accuracy 420 and this difference is statistically significant (CI of XAI is separated from that of Labeille & Chloé, p value of Ravni≠XAI is 0.014).

| | Accuracy 420 | | | | accuracy 95% CI | | | |
|---|---|---|---|---|---|---|---|---|
| | Labeille | Chloé | Ravni | XAI | Labeille | Chloé | Ravni | XAI |
| FotoFinder | 0.57 | 0.47 | 0.67 | 0.74 | 0.506-0.638 | 0.412-0.531 | 0.617-0.733 | 0.687-0.794 |
| Visiomed | 0.66 | 0.6 | 0.73 | 0.76 | 0.597-0.716 | 0.543-0.663 | 0.675-0.778 | 0.704-0.815 |
| HorusX30 | 0.53 | 0.53 | 0.66 | 0.73 | 0.469-0.597 | 0.465-10.589 | 0.601-0.716 | 0.679-0.786 |
| HorusX20 | 0.56 | 0.54 | 0.7 | 0.73 | 0.498-0.621 | 0.481-0.605 | 0.638-0.757 | 0.671-0.790 |
| combined dermoscope | 0.73 | 0.67 | 0.74 | 0.83 | 0.675-0.782 | 0.621-0.733 | 0.687-0.794 | 0.778-0.872 |

Remarks

Among 4 dermoscopes, dermatologists & XAI have highest accuracy 420 for Visiomed combined use of dermoscope improves accuracy 420.

p value is computed by two-tailed z-test, using statsmodels.stats.proportion.proportions_ztest

| p value | Labeille | Chloé | Ravni | XAI |
|---|---|---|---|---|
| FF vs Visiomed | 0.040 | 0.005 | 0.139 | 0.602 |
| FF vs HX30 | 0.362 | 0.204 | 0.848 | 0.838 |
| FF vs HX20 | 0.855 | 0.123 | 0.435 | 0.838 |
| FF vs combined | 0.000 | 0.000 | 0.092 | 0.016 |
| Visiomed vs HX30 | 0.003 | 0.12 | 0.094 | 0.468 |
| Visiomed vs HX20 | 0.026 | 0.2 | 0.482 | 0.468 |
| Visiomed vs combined | 0.094 | 0.11 | 0.838 | 0.057 |
| HX30 vs HX20 | 0.466 | 0.785 | 0.331 | 1.0 |
| HX30 vs combined | 0.000 | 0.002 | 0.061 | 0.009 |
| HX20 vs combined | 0.000 | 0.004 | 0.364 | 0.009 |

Accuracy 420 of Treatment for Separated and Combined Use of Dermoscope
Ground Truth:
  MEL, BCC, SCC, Paget: biopsy excision
  others: return M3

$$\text{Accuracy } 420 = (\text{\# correct treatment } dx)/(\text{\# images})$$

images=972 if consider all images
images=243 if consider separated or combined use of dermoscope
images=656 if consider biopsy excision
images=316 if consider return M3
95% CI is computed using bootstrap sampling with 1000 repetitions
Accuracy 420 on Each Category and on all Images

|  | Labeille | Chloé | Ravni | XAI |
|---|---|---|---|---|
| biopsy excision | 1.00 | 0.80 | 0.91 | 0.95 |
| return M3 | 0.13 | 0.61 | 0.40 | 0.56 |
| all images | 0.72 | 0.74 | 0.74 | 0.83 |
| all images 95% CI | 0.687-0.742 | 0.715-0.770 | 0.711-0.769 | 0.801-0.848 |

Accuracy 420 on Separated or Combined Use of Dermoscope

NaN values in the answer of dermatologists are replaced by biopsy excision

Treatment dx for combined use of dermoscopes is defined as follows:

if 4 answers contain only one category, the final answer is that category if 4 answers contain both categories, one of them with higher frequency, the final answer is the category with higher frequency if 4 answers contain both categories with the same frequency, the final answer is biopsy excision

| | Accuracy 420 | | | | accuracy 95% CI | | | |
|---|---|---|---|---|---|---|---|---|
| | Labeille | Chloé | Ravni | XAI | Labeille | Chloé | Ravni | XAI |
| FotoFinder | 0.75 | 0.72 | 0.74 | 0.82 | 0.700-0.807 | 0.663-0.774 | 0.683-0.790 | 0.778-0.868 |
| Visiomed | 0.71 | 0.77 | 0.75 | 0.83 | 0.650-0.770 | 0.716-0.819 | 0.700-0.807 | 0.786-0.877 |
| HorusX30 | 0.70 | 0.73 | 0.72 | 0.80 | 0.638-0.761 | 0.675-0.790 | 0.667-0.778 | 0.757-0.852 |
| HorusX20 | 0.70 | 0.76 | 0.74 | 0.84 | 0.638-0.753 | 0.700-0.807 | 0.691-0.794 | 0.798-0.889 |
| combined dermoscope | 0.70 | 0.78 | 0.75 | 0.83 | 0.634-0.749 | 0.724-0.831 | 0.695-0.798 | 0.782-0.881 |

| p value | Labeille | Chloé | Ravni | XAI |
|---|---|---|---|---|
| FF vs Visiomed | 0.308 | 0.177 | 0.756 | 0.812 |
| FF vs HX30 | 0.223 | 0.761 | 0.611 | 0.564 |
| FF vs HX20 | 0.223 | 0.303 | 1.0 | 0.547 |
| FF vs combined | 0.223 | 0.118 | 0.756 | 0.812 |
| Visiomed vs HX30 | 0.843 | 0.295 | 0.412 | 0.416 |
| Visiomed vs HX20 | 0.843 | 0.749 | 0.756 | 0.715 |
| Visiomed vs combined | 0.843 | 0.828 | 1.0 | 1.0 |
| HX30 vs HX20 | 1.0 | 0.468 | 0.611 | 0.239 |
| HX30 vs combined | 1.0 | 0.207 | 0.412 | 0.416 |
| HX20 vs combined | 1.0 | 0.591 | 0.756 | 0.715 |

Figure 5:
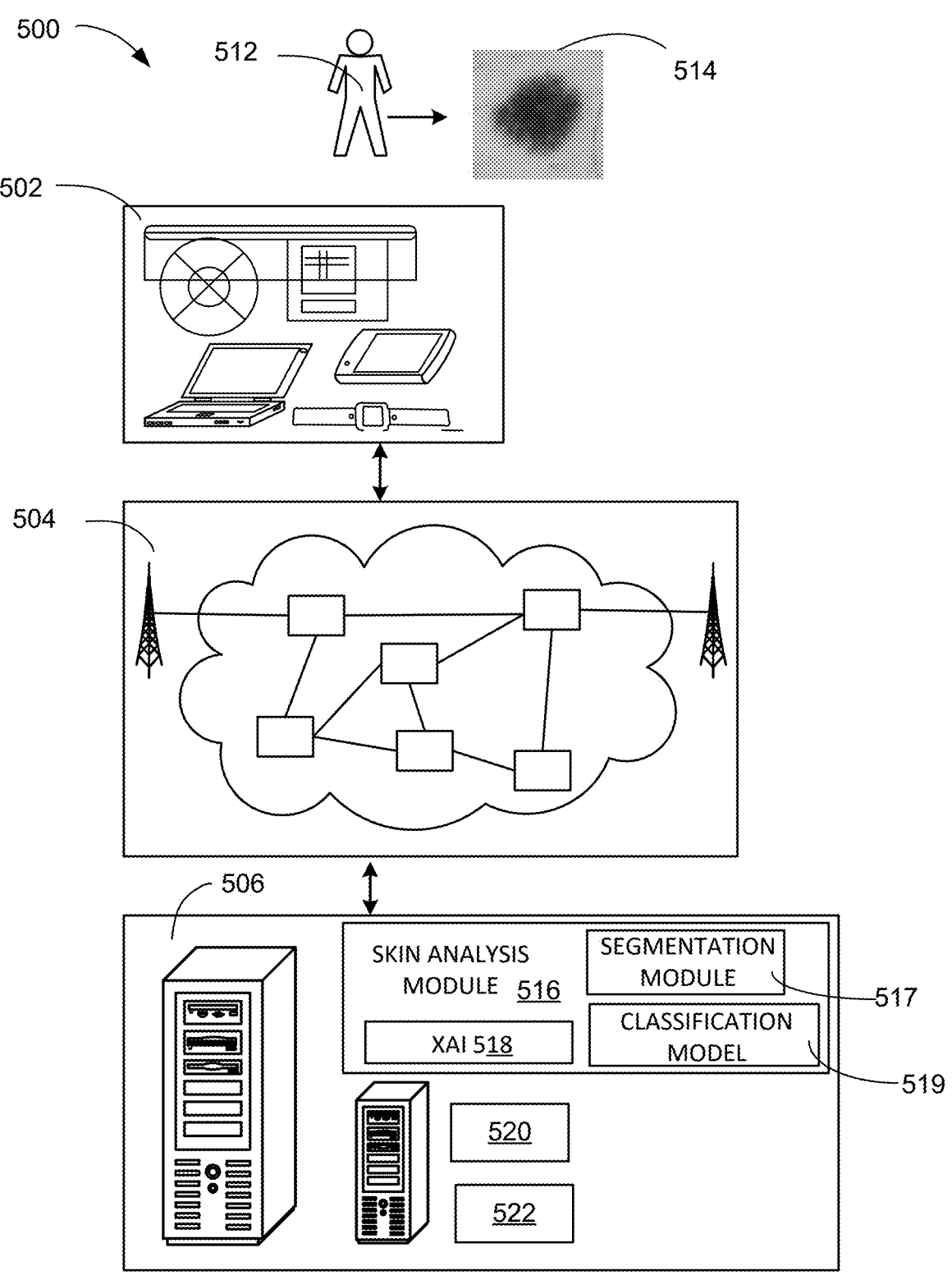
FIG. 5 is an example of a system architecture diagram of a compute system with an image based skin cancer detection mechanism in an embodiment of the present invention.

Referring now to FIG. 5, therein is shown an example of a system architecture diagram of a compute system 500 with an acne diagnostic mechanism in an embodiment of the present invention. Embodiments of the compute system 500 provide standardized and objective skin cancer detection across 10 classifications and 122 sub-classes, as described earlier. The 10 classifications include:

MEL: including all types of malignant melanoma such as melanoma in situ, superficial spreading melanoma, nodular melanoma, etc.

BCC: including all types of basal cell carcinoma such as superficial basal cell carcinoma, nodular basal cell carcinoma, basosquamous carcinoma, ulcerated basal cell carcinoma, etc.

EPI: including all types of epidermal pre-malignant and malignant tumors such as actinic keratosis, Bowen disease, squamous cell carcinoma, etc.

MALO: including malignant lesions that are not in MEL, BCC and EPI. This class contains Merkel cell carcinoma, kaposi sarcoma, dermatofibrosarcoma protuberans, etc.

NV: including all types of melanocytic nevus and melanosis.

DF: including all types of dermatofibroma

BAL: including all types of benign adnexal or appendage lesions, such as cystic lesions, pilomatricoma, adenoma, poroma, etc.

BKL: including all types of benign keratinocytic lesions and lentigines such as solar lentigo, seborrheic keratosis, lichen planus-like keratosis, clear cell acanthoma, etc.

VASC: including all types of benign vascular lesions and haemorrhages.

BENO: including all benign 316 lesions that are not in NV, DF, BAL, BKL and VASC.

In examples of embodiment of classification system, malignant 318 lesions are covered in four classes: MEL, BCC, EPI, MALO, while benign 316 lesions are covered in six classes: NV, DF, BKL, VASC, BAL, BENO. Moreover, special sub-classes are separated from others to facilitate the estimation of cancer risk level. For example, Spitz nevus is separated from other benign nevi in the class NV. Pyogenic granuloma is also separated from other benign vascular lesions in the class VASC.

The compute system 500 can include a first device 502, such as a client or a server, connected to a second device 506, such as a client or server. The first device 502 can communicate with the second device 506 through a network 504, such as a wireless or wired network.

For example, the first device 502 can be of any of a variety of computing devices, such as a smart phone, a tablet, a cellular phone, personal digital assistant, a notebook computer, a wearable device, internet of things (IoT) device, or other multi-functional device. Also, for example, the first device 502 can be included in a device or a sub-system.

The first device 502 can couple, either directly or indirectly, to the network 504 to communicate with the second device 506 or can be a stand-alone device. The first device 502 can further be separate form or incorporated with a vehicle, such as a car, truck, bus, motorcycle, or a drone.

For illustrative purposes, the compute system 500 is described with the first device 502 as a mobile device, although it is understood that the first device 502 can be different types of devices. For example, the first device 502 can also be a non-mobile computing device, such as a server, a server farm, cloud computing, or a desktop computer.

The second device 506 can be any of a variety of centralized or decentralized computing devices. For example, the second device 506 can be a computer, grid computing resources, a virtualized computer resource, cloud computing resource, routers, switches, peer-to-peer distributed computing devices, or a combination thereof.

The second device 506 can be centralized in a single room, distributed across different rooms, distributed across different geographical locations, embedded within a telecommunications network. The second device 506 can couple with the network 504 to communicate with the first device 502. The second device 506 can also be a client type device as described for the first device 502.

For illustrative purposes, the compute system 500 is described with the second device 506 as a non-mobile computing device, although it is understood that the second device 506 can be different types of computing devices. For example, the second device 506 can also be a mobile computing device, such as notebook computer, another client device, a wearable device, or a different type of client device.

Also, for illustrative purposes, the compute system 500 is described with the second device 506 as a computing device, although it is understood that the second device 506 can be different types of devices. Also, for illustrative purposes, the compute system 500 is shown with the second device 506 and the first device 502 as endpoints of the network 504, although it is understood that the compute system 500 can include a different partition between the first device 502, the second device 506, and the network 504. For example, the first device 502, the second device 506, or a combination thereof can also function as part of the network 504.

The network 504 can span and represent a variety of networks. For example, the network 504 can include wireless communication, wired communication, optical, ultrasonic, or the combination thereof. Satellite communication, cellular communication, Bluetooth, Infrared Data Association standard (IrDA), wireless fidelity (WiFi), and worldwide interoperability for microwave access (WiMAX) are examples of wireless communication that can be included in the communication path. Ethernet, digital subscriber line (DSL), fiber to the home (FTTH), and plain old telephone service (POTS) are examples of wired communication that can be included in the network 504. Further, the network 504 can traverse a number of network topologies and distances. For example, the network 504 can include direct connection, personal area network (PAN), local area network (LAN), metropolitan area network (MAN), wide area network (WAN), or a combination thereof.

Returning to the description standardized and objective acne scoring of the embodiments of the compute system 500, as an example, the compute system 500 provide functions to various users 512, including patients and clinicians. The compute system 500 can provide functions to the users 512 in a number of ways.

For example, the compute system 500 can provide the functions for the users 512 with the first device 502, the second device 506, distributed between these two devices, or a combination thereof. Also, as examples, the compute system 500 can provide a mobile applications for the patients, the clinicians, or a combination thereof. Further as an example, the compute system 500 can provide the functions via a web-browser based applications or a software to be executed on the first device 502, the second device 506, distributed between these two devices, or a combination thereof.

In one embodiment as an example, patient images 514 are taken and uploaded by the patient and reviewed by an explainable artificial intelligence (XAI) module 518 and the clinician. The XAI module 518 can be a specialized hardware structure that executes a specialized software, such as the XAI model 200, for analysis of the skin lesions 104 of FIG. 1. In this embodiment, a patient launches the image based skin cancer detection mechanism via the mobile application and logs into the patient's account. The patient can be prompted to upload or take images as the patient images 514. The compute system 500 can guide a patient on photo guidelines for the patient images 514 and accepts or rejects the patient images 514 for retake based on a pre-specified criteria, e.g., distance, quality, blur, or a combination thereof. The patient images 514 can be selected and processed based on the images uploaded by the user 512.

Once the patient images 514, as required for analysis, are successfully uploaded, the compute system 500 can send or load the patient images 514 to a skin analysis module 516 for analysis. The skin analysis module 516 can include a segmentation module 517. The segmentation module 517 can be a hardware structure managed by software that can identify the perimeter of a lesion identified in the patient image 514 in order to standardize the images being processed. The explainable artificial intelligence (XAI) module 518 can be a machine learning processor or artificial intelligence structure configured to analyze the images provided by the segmentation module 517 and to generate a classification model 519 to identify a skin lesion classification 520 and a risk level assessment 522. For brevity and clarity and as an example, the XAI module 518 is shown in FIG. 5 as being executed in the second device 506 although it is understood that portions can operate on the first device 502, such as the mobile app or the web-browser based application, can operate completely on the first device 502, or a combination thereof. As a further example, the XAI module 518 can be implemented in software running on specialized hardware, full hardware, or a combination thereof.

The risk level assessment 522 can include a risk level of zero indicating no cancer risk was detected. The risk level assessment 522 of risk level one indicating a precautionary warning, but not active cancer was detected. The risk level assessment 522 can include a risk level two indicating a minor detection of cancer or pre-cancer was detected. The risk level assessment 522 can include a risk level three indicating the detection of a significant risk of cancer has been detected. The risk level assessment 522 can include a risk level four can indicate a risk of melanoma in situ and or non-melanoma skin cancer. The risk level assessment 522 can also include a risk level five indicating a high risk of invasive melanoma or other high grade skin cancers.

Based on analysis results, the compute system 500 can display information to the patient including a recommendation based on the patient images 514, uploaded, for the patient to schedule a visit with your primary care physician or with a specialist based on the skin lesion classification 520, which may or may not be visible or displayed to the user 512.

If the XAI module 518 provides the skin analysis module 516 with an indication below a pre-specified level of the risk level assessment 522, the compute system 500 can display a message that based on the patient images 514, uploaded, the user 512 may not need a visit with their primary care physician or with other specialists. The compute system 500 can provide a function allowing the user 512 to schedule a visit with the clinician. The classification model 519 can be a machine learning structure configured to define the criteria for detecting the skin lesion classification 520. The classification model 519 can include a convolutional neural network 519 already trained.

Continuing the example, the compute system 500 can provide a function that allows the clinician to access the patient images 514 uploaded by the user 512 and the skin lesion classification 520, such as the MEL, BCC, EPI, or MALO, through the web-based dashboard from the image based skin cancer detection mechanism. The compute system 500 allows the clinician to make edits to annotations determined by the XAI module 518 and the risk level assessment 522 and saves the results. The clinician can utilize the skin lesion classification 520 to make the diagnostic decision and takes necessary treatment steps (if applicable).

In a further embodiment as an example, the compute system 500 can allow a patient to schedule a visit with a primary care physician or with a specialist. A clinician can launch the image based skin cancer detection mechanism, such as a mobile application and logs in. The compute system 500 can be prompted to upload or take the patient images 514 of the patient's body or body parts to be analyzed by the XAI module 518.

The compute system 500 can provide guidance to the clinician on the photo guidelines. The compute system 500 can accept or reject images for retake based on a pre-specified criteria, such as distance, quality, blur, or a combination thereof. Once the patient images 514 are success-fully uploaded, the compute system 500 and send or load the patient images 514 to the XAI module 518 for analysis.

Continuing the example, the compute system 500 can similarly provide a function that allow the clinician to access the patient images 514, uploaded by the user 512, and the skin lesion classification 520, such as with the web-based dashboard from the image based skin cancer detection mechanism. The compute system 500 allows the clinician to make edits to annotations determined by the XAI module 518 and the risk level assessment 522 (if necessary) and saves the results. The clinician can utilize the skin lesion classification 520 to make the diagnostic decision and takes necessary treatment steps (if applicable).

Figures 6, 7:
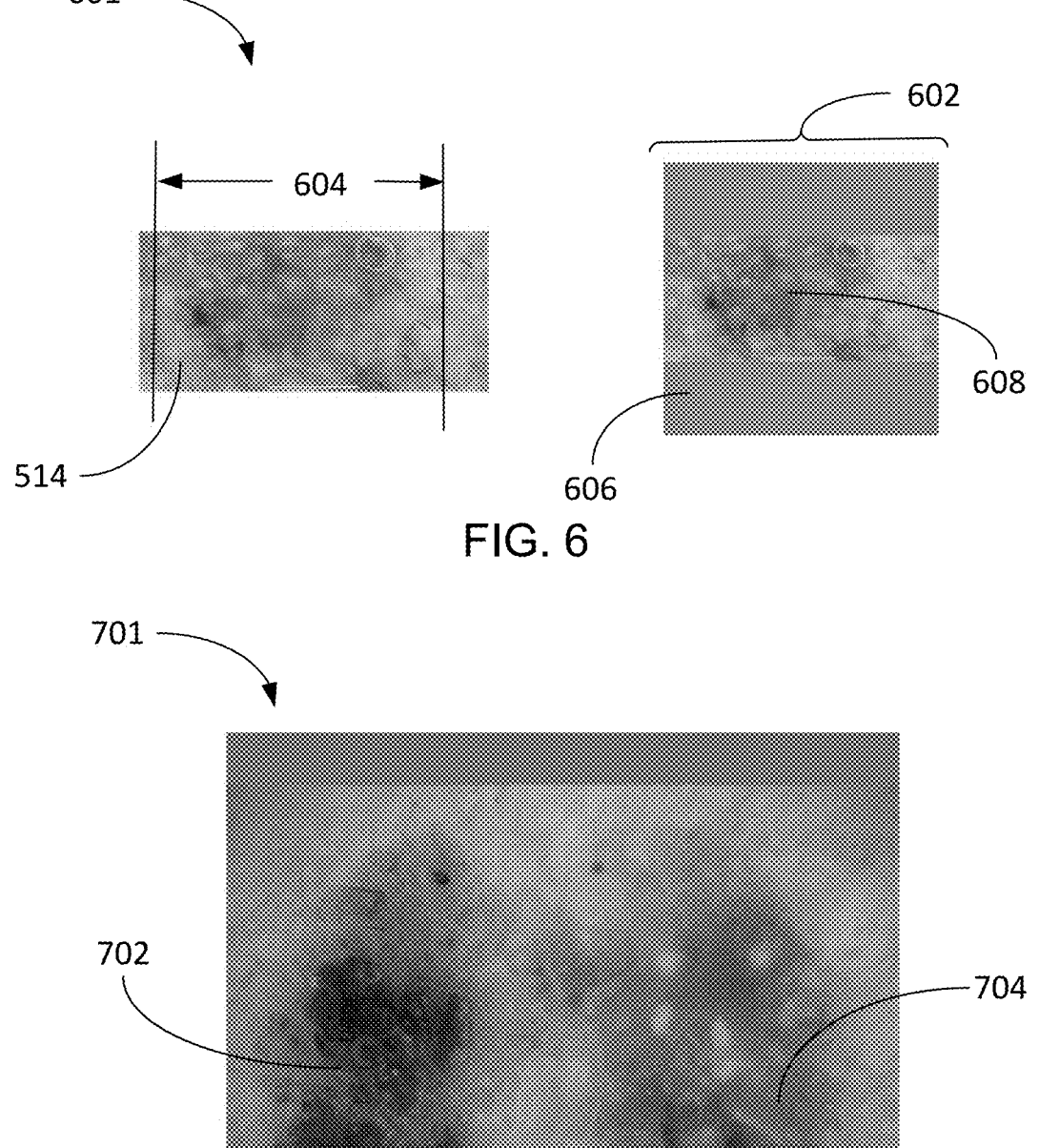
FIG. 6 is an example of center cropping and padding for skin lesion classification in an embodiment.
FIG. 7 is an example of a normalized image with a collision of dermoscopic images between two classifications of skin cancer BCC and BKL.

Referring now to FIG. 6, therein is shown an example of center cropping and padding 601 for the skin lesion classi-fication 520 of FIG. 5 in an embodiment. The compute system 500 of FIG. 5, the XAI module 518 of FIG. 5, or a combination thereof can process the patient images 514, such as the leftmost image depicted in FIG. 6. The rightmost image depicted in FIG. 6 is an example of a normalized image 602 that has been center-cropped 604 and padding 606 for analysis.

The segmentation module 517 of FIG. 5 is a hardware structure managed by software and trained on the patient images 514 to automatically detect and segment a skin lesion 208. The segmentation module 517 identifies the perimeter of the skin lesion 208. Then the patient images 514 are center-cropped 604 around the segmented skin lesion 608 with a certain margin, so that the skin lesion 608 lies at the center (see FIG. 5). Average color of the padding 606 might be performed afterward to obtain square images. The combination of the segmentation, center-cropped 604 and the padding 606 is identified as the normalized image 602. The EfficientNetB4 can be utilized with the center-cropped 604 size of 384 pixels by 384 pixels and pretrained weight on ImageNet. The segmentation module 517 of FIG. 5 was trained using NVDIA Titan RTX with starting learning rate 0.0003, learning rate scheduler is the multiplication of starting learning rate and the rate decay (which is 0.985) powers epoch. The segmentation module 517 was trained using ISIC dataset. The trained segmentation module 517 is used to predict on all dataset to obtain a normalized dataset for the classification model 519.

Referring now to FIG. 7, therein is shown an example of a normalized image 701 with a collision of dermoscopic images between two classifications of skin cancer BCC and BKL. An example of the display shown on the display in an embodiment can be on the first device 502 of FIG. 5, the second device 506 of FIG. 5, or a combination thereof. The normalized image 701 can include the padding 606 in order to establish the standard size of 384 pixels by 384 pixels.

In this example, the normalized image 701 of the collision of dermoscopic images is shown with the benign lesions of the keratosis type, solar lentigines, seborrheic keratoses, and lichen-planus like keratosis (bkl) 702 adjacent to a basal cell carcinoma 704. In this example, the input is the normalized image 701 including the collision of dermoscopic images as the patient image 514 to the compute system 500, the XAI module 518, or a combination thereof.

The configuration of classification model 519 of FIG. 5 is trained to classify a given one of the skin lesion 608 of FIG. 6 into 10 different classes as MEL, BCC, EPI, MALO, NV, DF, BAL, BKL, VASC, or BENO. The classification model 519 can handle multi-label problem that is one image that can belong to two or more classes (collision), type of images that is dermoscopic, macro, or irrelevant. The classification model 519 was trained on normalized images using class and sub-class label. The classification model 519 has a multiplication step (between outputs of class and sub-class prediction) to obtain the final sub-class prediction. The multiplication step is a specific design in order to obtain a more consistent result, in particular, the sub-class prediction output could not exceed the output of class prediction. An improved class prediction can be achieved because the model is forced to learn important features of the sub-class. Sigmoid activation function can be used before output layers are identified because the model can classify one image into more than one class (in collision cases). Since the number of collision images is very low (about 0.38% in our dataset), we create synthetic collision images by putting two images next together in order to verify the identification ability of the classification model 519.

Figure 8:
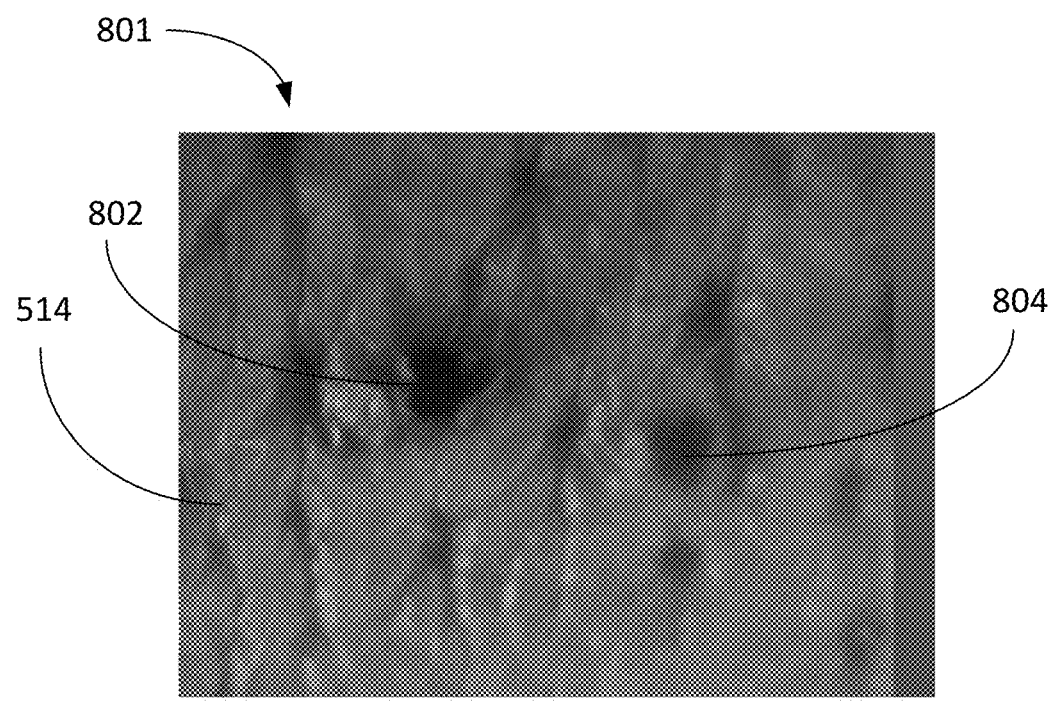
FIG. 8 is an example of the patient image with the collision of dermoscopic images between two classifications of skin cancer identified as BCC and VASC.

Referring now to FIG. 8, therein is shown an example of the patient image 514 with the collision of dermoscopic images 801 between two classifications of skin cancer identified as BCC and VASC. In this example, the patient image 514 can be depicted with the skin lesion classification 520 of FIG. 5 and can be identified by the compute system 500 of FIG. 5, the XAI module 518 of FIG. 5, or a combination thereof.

Vascular tumors 802 can be a type of tumor that forms from cells that make blood vessels or lymph vessels. The vascular tumors (VASC) 802 may be benign 316 (not cancer) or malignant 318 (cancer) and can occur anywhere in the body. The vascular tumors 802 may form on the skin, in the tissues below the skin, and/or in an organ. A basal cell carcinoma (BCC) 804 can also be present, which can indicate cancer or pre-cancer.

The compute system 500, the XAI module 518, or a combination thereof can be trained to identify each sub-class individually. Once the classification model 519 of FIG. 5 can identify metrics that are greater or higher than a pre-defined threshold for each sub-class, the classification model is considered to be trained. For example, having a Jaccard score higher than 0.8, the compute system 500, the XAI module 518, or a combination thereof can be considered to be trained, tested, or a combination thereof as the whole system together. In this training process, a test set is not part of the training set. The test set can include a variety of data for example different skin tone, different cancer types, different resolution, etc. Every time, if any portion of the compute system 500, the XAI module 518, or a combination thereof can provide an update, which can be from one model, from one algorithm, the compute system 500, the XAI module 518, or a combination thereof can predict the skin lesion classification 520 on those images by running through the image based skin cancer detection mechanism. After the raw results, the compute system 500, the XAI module 518, or a combination thereof can run statistical tests and compare the analysis result with the one of the previous version. If the result is better, the compute system 500, the XAI module 518, or a combination thereof can keep the update. Otherwise, it is not used.

Regarding Jaccard score, the Jaccard index, also known as the Jaccard similarity coefficient, is a statistic used for gauging the similarity and diversity of sample sets. It measures the similarity between finite sample sets, it is defined as the ratio of the intersection over the union of the two sets.

$$J(A, B) = \frac{|A \cap B|}{|A \cup B|} \tag{2.4}$$

Figure 9:
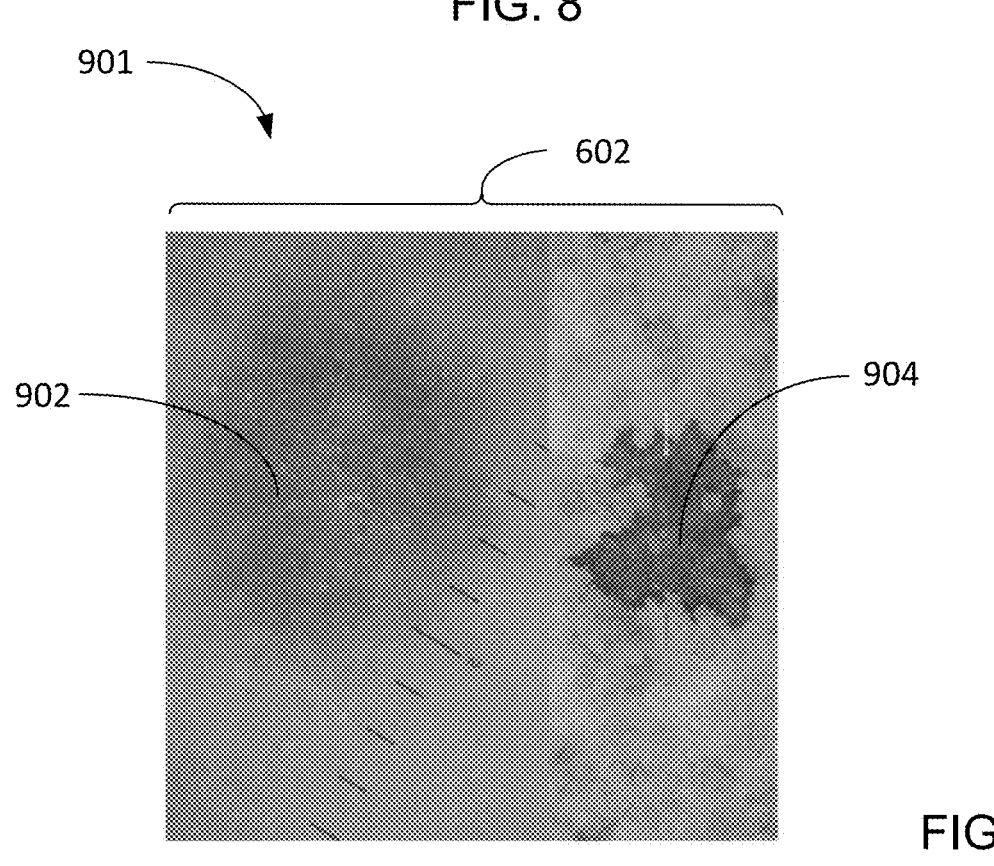
FIG. 9 is an example of the normalized image with a collision of dermoscopic images between two classifications of skin cancer identified as DF and BKL.

Referring now to FIG. 9, therein is shown an example of the normalized image 602 with a collision of dermoscopic images 901 between two classifications of skin cancer identified as DF and BKL. The collision of dermoscopic images 901 depicts the dermatofibroma (DF) 902 and benign keratinocytic lesions (BLK) 904 and can be classified by the compute system 500 of FIG. 5, the XAI module 518 of FIG. 5, or a combination thereof.

Figure 10:
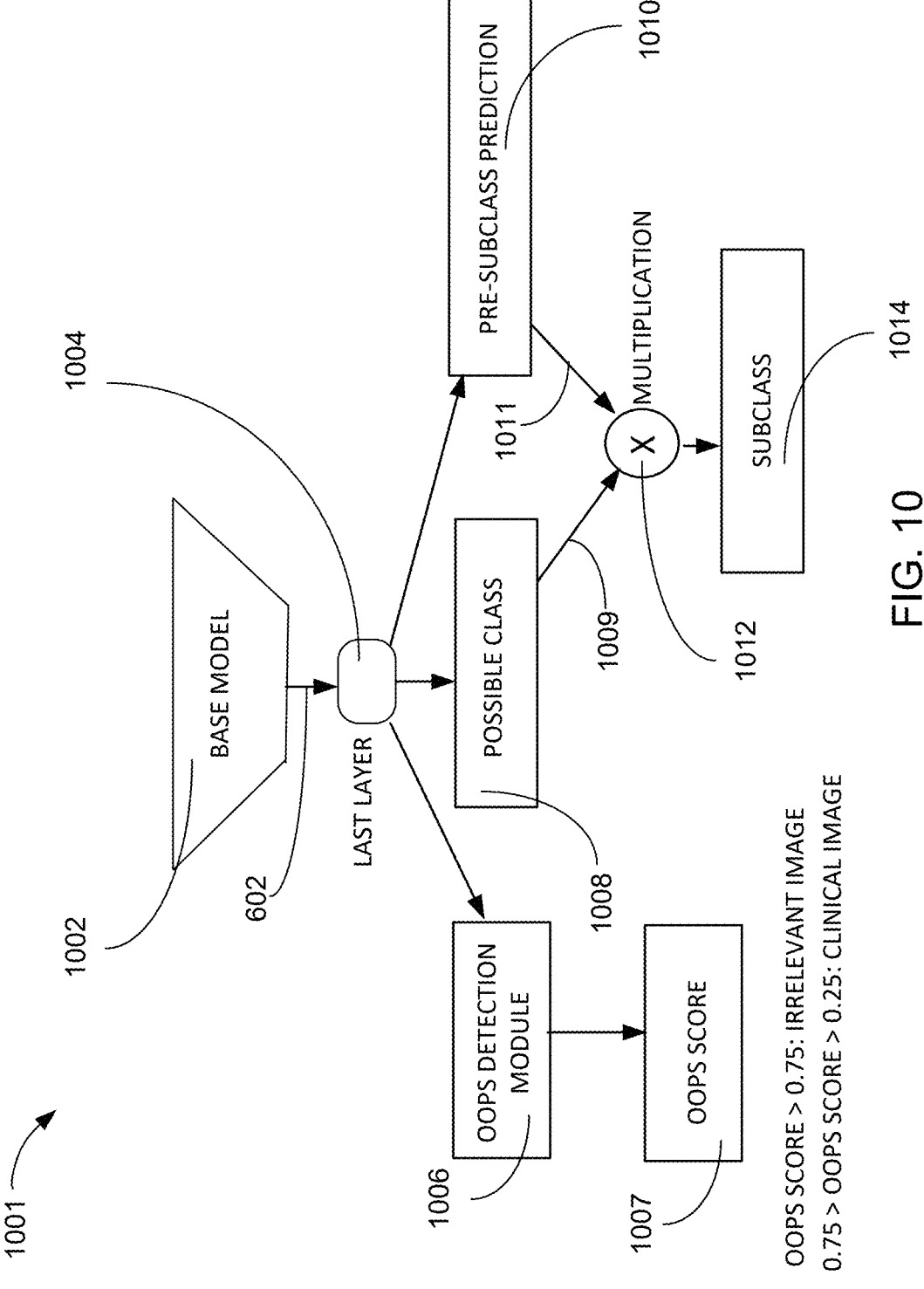
FIG. 10 is a functional block diagram of the classification model in sub-class-based approach in an embodiment.

Referring now to FIG. 10, therein is shown a functional block diagram 1001 of the classification model 519 in sub-class-based approach in an embodiment. The functional block diagram 1001 depicts a base model 1002 producing a last layer 1004. The training pipeline contains two major steps: segmentation and classification. The classification model 519 is not directly trained on the patient images 514 of FIG. 5 because: the skin lesion 608 of FIG. 6 might be too small compared with the rest part of the patient image 514, the skin lesion 608 might be displaced off-center, and other details than the skin lesion 608 might confuse the classification model 519. Therefore, the base model 1002 first runs the segmentation module 517 of FIG. 5 then center-crop the detected skin lesion 608 in order to generate the normalized image 602. The classification model 519 can operate on the normalized image 602 to produce the last layer 1004.

In this example, the flow can progress from an oops detection module 1006 to produce an oops score 1007. Continuing the example, the oops detection module 1006 can perform an image quality check and can function as a filter for preventing bad quality images to be used as input for the classification model 519. The oops score 1007 can indicate the quality of images that are too blurry or images that are of poor luminosity (either too bright, too dark or too noisy). The oops score 1007 greater that 0.75 indicates the normalized image 602 is irrelevant and should not be used for analysis. The oops score 1007 that is less than or equal to 0.75 an greater than 0.25 indicates a clinical image that is acceptable for analysis by the classification model 519. It is also determined that the oops score 1007 less than or equal to 0.25 indicated the normalized image 602 is acceptable for training the classification model 519.

For example, the oops detection module 1006 can check the patient images 514 of FIG. 5 that are input for certain quality criteria and meeting or exceeding a quality threshold. As a specific example, if an instance of the patient images 514 is relevant or usable to compute the skin analysis module 516, then the oops detection module 1006 determined that instance of the normalized images 602 continues processing.

The classification model 519 was trained using ISIC dataset. For the ISIC dataset, with the help from doctors, about 30% have sub-class labels. Moreover, there are several duplicate images in ISIC dataset, which can be identified by the classification model 519 to find all possible duplicates of the normalized images 602.

The last layer 1004 can be coupled to a class estimation module 1008 and a pre-sub-class prediction module 1010. The class estimation module 1008 can be a hardware structure configured to estimate the class of the skin lesion 608 in the normalized images 602. The class estimation module 1008 can calculate a class prediction 1009, for indicating the class of the skin lesion 608 identified in the normalized image 602. The pre-sub-class estimation module 1010 can be a hardware structure configured to match the normalized image 602 with a sub-class prediction 1011. The output of the class estimation module 1008 and the pre-sub-class prediction module 1010 can be inputs to a multiplier 1012 that can produce a sub-class 1014 that corresponds to each of the class prediction 1009.

The multiplier 1012 can be a hardware structure configured to multiply the class prediction 1009 with the sub-class prediction 1011 in order to obtain a more consistent result. The classification model 519 is taught to identify important features in the normalized images 602 to correctly identify the class prediction 1009 and the sub-class prediction 1011. The classification model can also identify any duplicates of the normalized images 602 in the training dataset and the validation dataset.

It has been discovered that the use of the multiplier 1012 can improve the reliability of the class prediction 1009 and the sub-class prediction 1011 across the normalized images 602. The improved reliability of the classification model 519 can be demonstrated by a comparison of the detection capabilities of the compute system 500 of FIG. 5, the XAI module 518 of FIG. 5, or a combination thereof.

Figures 11, 12:
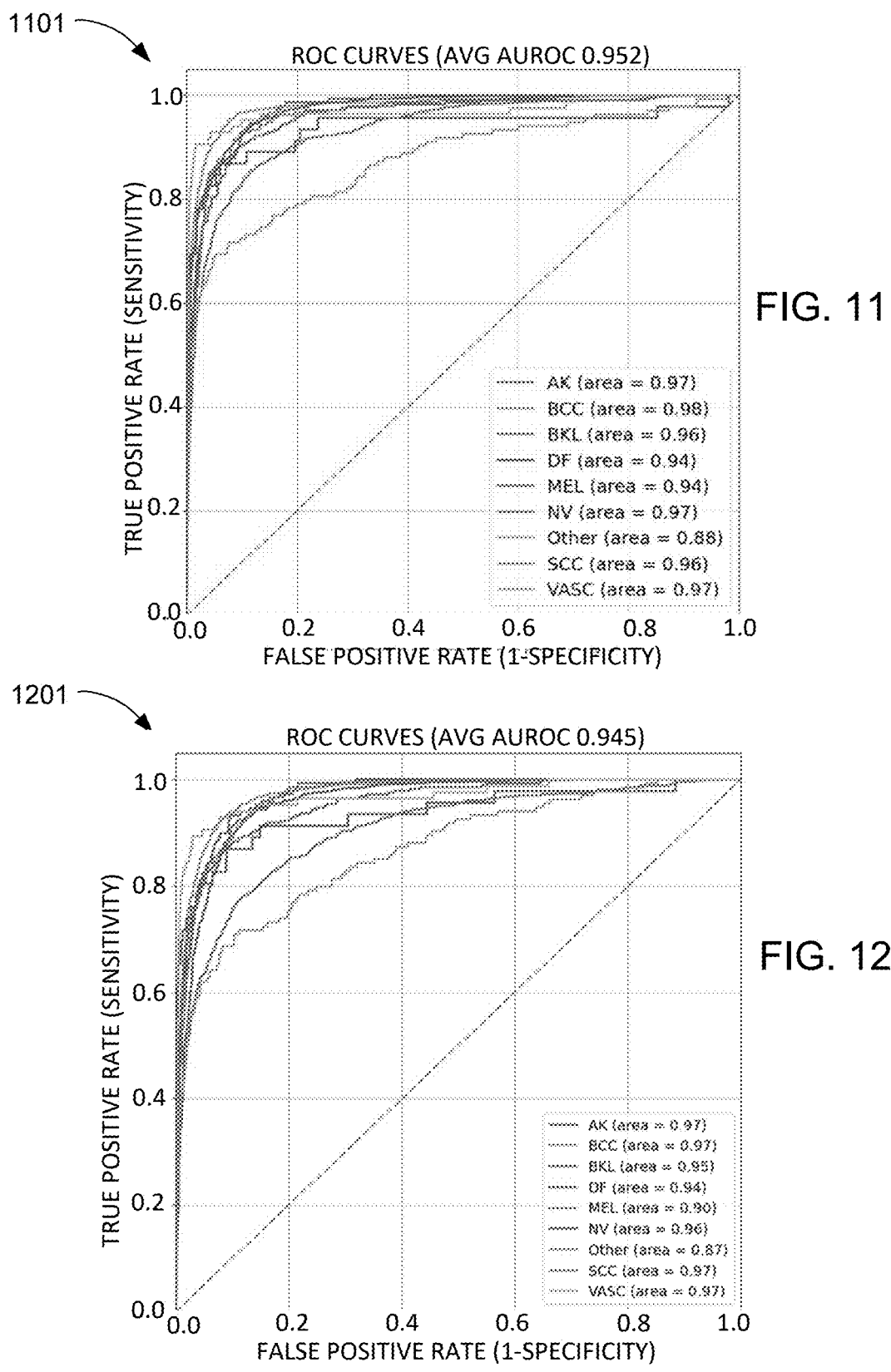
FIG. 11 is an example of a receiver operating characteristic (ROC) validation curve for each skin lesion classification.
FIG. 12 is an example of a receiver operating characteristic (ROC) validation curve for each of the skin lesion classification with sub-class label training.

Referring now to FIG. 11, therein is shown an example of a receiver operating characteristic (ROC) validation curve 1101 for each of the skin lesion classification 520. The compute system 500, the XAI module 518, or a combination thereof can be implemented in an number of ways. For example, the oops module 1006 of FIG. 10 can be implemented with an Inception-ResNet-v2 convolutional neural network, which was pre-trained with the ImageNet data set, for the encoding part.

A blind test of the XAI module 518 has been applied to 4926 dermatoscopic skin images collected by the Trieste team during their practice. The Trieste test set was classified into nine classes: MEL, BCC, SCC, AK, NV, BKL, DF, VASC, and Other. The test results are summarized in Table A. A sensitivity of 93% (resp. 80%) and a specificity of 70% (resp. 92%) for MEL when using the cutoff threshold of 0.18 (resp. 0.50).

A threshold of 0.18 for MEL means that any image with MEL score above 0.18 is considered to have significant melanoma risk. Test results compare favorably to the performance of dermatologists. The sensitivity-specificity of dermatologists for dematoscopic image-based melanoma detection is only sensitivity of 67%-specificity of 62% versus the XAI module 518 sensitivity of 93%-specificity of 70%.

TABLE A

| | | | | | Summary of validation result on the ItoBos test set | | | | | |
|---|---|---|---|---|---|---|---|---|---|---|
| Class | MEL | MEL | BCC | SCC | AK | NV | BKL | DF | VASC | Other |
| # Images | 868 | 868 | 697 | 211 | 148 | 2422 | 283 | 46 | 85 | 134 |
| AUROC | 0.94 | 0.94 | 0.98 | 0.96 | 0.97 | 0.97 | 0.96 | 0.94 | 0.97 | 0.88 |
| Sens (%) | 93 | 80 | 95 | 88 | 84 | 75 | 80 | 70 | 89 | 86 |
| SPEC (%) | 70 | 92 | 92 | 93 | 93 | 97 | 97 | 99 | 98 | 67 |
| THRESHOLD | 0.18 | 0.5 | 0.18 | 0.18 | 0.18 | 0.82 | 0.49 | 0.18 | 0.18 | 0.06 |

The results shown in Table A indicate a high reliability of the performance of the XAI module 518 in processing a validation data set. The performance of the XAI module 518 can out perform a clinician in most cases.

Referring now to FIG. 12, therein is shown an example of a receiver operating characteristic (ROC) validation curve 1201 for each of the skin lesion classification 520 with sub-class label training. The ROC curves 1201 and AUROC for each class model trained with sub-class label. It has been discovered that the model trained with sub-class label has higher average AUROC and better performance.

The training data set includes approximately 30% of the normalized images 602 of FIG. 6 include sub-class labels. By training the XAI module 518 of FIG. 5 with the sub-class labels can provide increased reliability of the detection of the skin lesion classification 520 of FIG. 5.

Figures 13, 14:
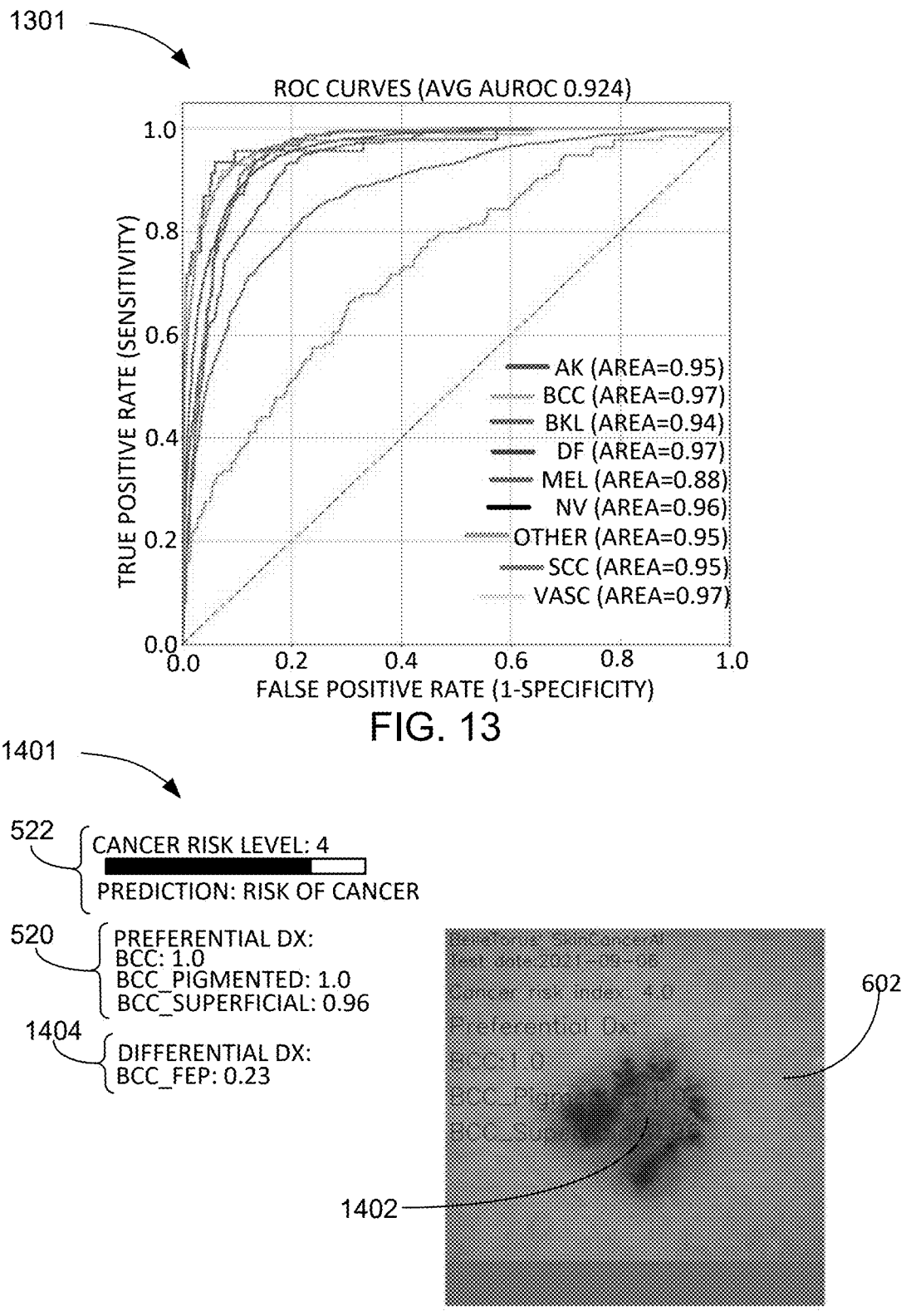
FIG. 13 is an example of a receiver operating characteristic (ROC) validation curve for each of the skin lesion classification without sub-class label training.
FIG. 14 is an example of a skin lesion display for analysis of basal cell carcinoma as performed by explainable AI (XAI) module in an embodiment.

Referring now to FIG. 13, therein is shown is an example of a receiver operating characteristic (ROC) validation curve 1301 for each of the skin lesion classification without sub-class label training.

The compute system 500 of FIG. 5 with the image based skin cancer detection mechanism, has the following three distinctive features: a large, diversified learning dataset of about 100 thousand images, a granular hierarchical class/sub-class classification, and innovative loss functions. The hierarchical classification system helps the XAI module 518 of FIG. 5 learn better and become more robust. The XAI module 518 that can detect not only 10 different classes included MEL, BCC, EPI, MALO, NV, DF, BAL, BKL, VASC and BENO but also 122 sub-class for example Melanoma in situ, Melanoma nodular, etc. We use hierarchical learning (class and sub-class) which gives more accurate result then training with class information only. The system includes two steps: segmentation of the skin lesion 608 of FIG. 6 and classification of the skin lesion 608. With this type of learning, each of the skin lesion 608 has two labels, one for class and the other for sub-class (or sub-type). If the skin lesion 608 does not have sub-class information, we will set the gradient be zero so that it will not affect the back-propagation process. A blind test using a test set of 4926 images provided an average of 0.95 of AUC (area under the curve) and 0.94 for MEL, 0.97 for NV, and 0.98 for BCC.

Referring now to FIG. 14, therein is shown an example of a skin lesion display 1401 for analysis of basal cell carcinoma 1402 as performed by the explainable AI (XAI) module 518 of FIG. 5 in an embodiment. The compute system 500 of FIG. 5, the XAI module 518, or a combination thereof can be trained for 95 epochs with substantially 40000 images in each epoch, about 80% of the data set is reserved for training set and 20% of the data set is for validation.

The analysis of the normalized image 602 of basal cell carcinoma 1402 as performed by the XAI module 518 depicts the risk level assessment 522, the skin lesion classification 520, and a skin lesion sub-class 1404. The risk level assessment 522 can indicate a level four indication provides a significant risk of pre-cancer or potential early cancer that should be addressed by a clinician. Optionally, the risk level assessment 522 and the skin lesion classification 520 can be displayed in the normalized image 602.

Referring now to FIG. 15, therein are shown examples of a skin lesion display 1501 for analysis of an alternate form of basal cell carcinoma 1502 as identified by the XAI module 518 of FIG. 5 in an embodiment. The normalized image 602 has a complete analysis of the basil cell carcinoma 1502 as predicted by the XAI module 518.

The analysis of the normalized image 602 of basal cell carcinoma 1502 as performed by the XAI module 518 depicts the risk level assessment 522, the skin lesion classification 520, and the skin lesion sub-class 1404. The risk level assessment 522 can indicate a level five indication provides a high risk of cancer that should be addressed by a clinician. Optionally, the risk level assessment 522 and the skin lesion classification 520 can be displayed in the normalized image 602.

Referring now to FIG. 16, therein are shown an example of a skin lesion display 1601 for analysis of a Melanoma cancer 1602 as performed by the explainable AI (XAI) module 518 of FIG. 5 in an embodiment. The normalized image 602 has a complete analysis of the melanoma cancer 1602 as predicted by the XAI module 518.

The analysis of the normalized image 602 of the melanoma cancer 1602 as performed by the XAI module 518 depicts the risk level assessment 522, the skin lesion classification 520, and the skin lesion sub-class 1404. The risk level assessment 522 can indicate a level four indication provides a substantial risk of cancer that should be addressed by a clinician. Optionally, the risk level assessment 522 and the skin lesion classification 520 can be displayed in the normalized image 602.

Figure 17:
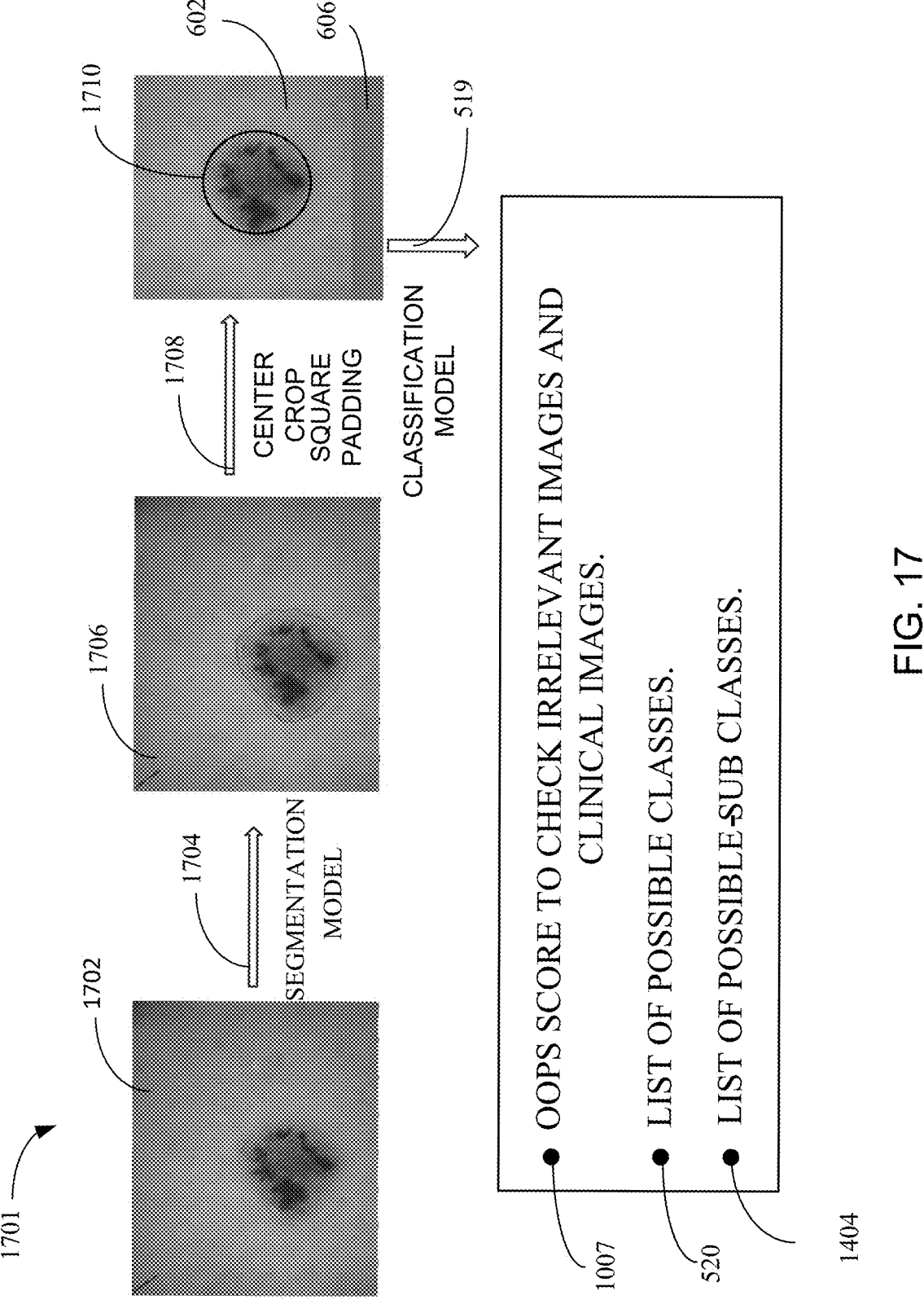
FIG. 17 is an example of a flow diagram of a skin cancer analysis in an embodiment.

Referring now to FIG. 17, therein are shown an example of a flow diagram 1701 of a skin cancer analysis in an embodiment. The flow diagram 1701 depicts generating an oops score in a block 1702, which is processed through a segmentation module 1704 to produce a segmented image 1706. The segmented image 1706 can be processed by a center crop and padding process 1708 to produce the normalized image 602 including the skin lesion 608 at the center 1710 and the padding 606. The normalized image 602 is then submitted to the XAI module 518 of FIG. 5 for generating skin lesion classification 520 of FIG. 5. The classification model 519 can provide the oops score 1007, the list of possible classes 520, and list of possible sub-classes 1404.

Figure 18:
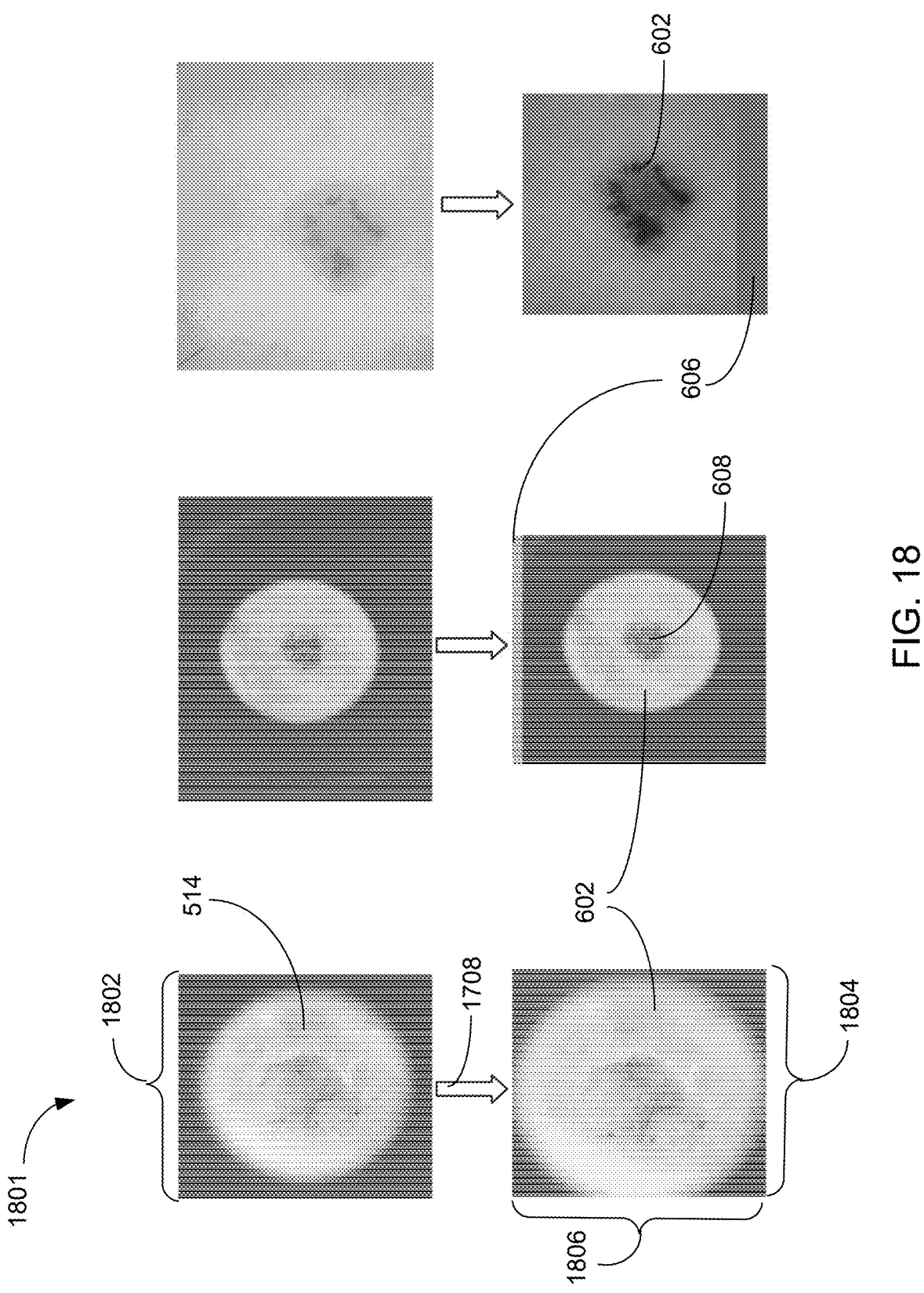
FIG. 18 is an example of an image center crop and padding process in an embodiment.

Referring now to FIG. 18, therein is shown an example of an image center crop and padding process 1801 in an embodiment. The production of the normalized images 602 relies on the center crop and padding process 1708. An input width 1802 can be below the standard size of the normalized images 602. The center crop and padding process 1708 can adjust the input width 1802 to match the normalized width 1804 of 384 pixels. The center crop and padding process 1708 also adjusts the normalized height 1806 to match the normalized width 1804.

In case the patient image 514 is larger than the normalized image 602, the center crop and padding process 1708 can crop the patient image 514 in order to meet the normalized width 1804 and add the padding 606 to establish the normalized height 1806 with the skin lesion 608 at the center 1710 of FIG. 17.

Figure 19:
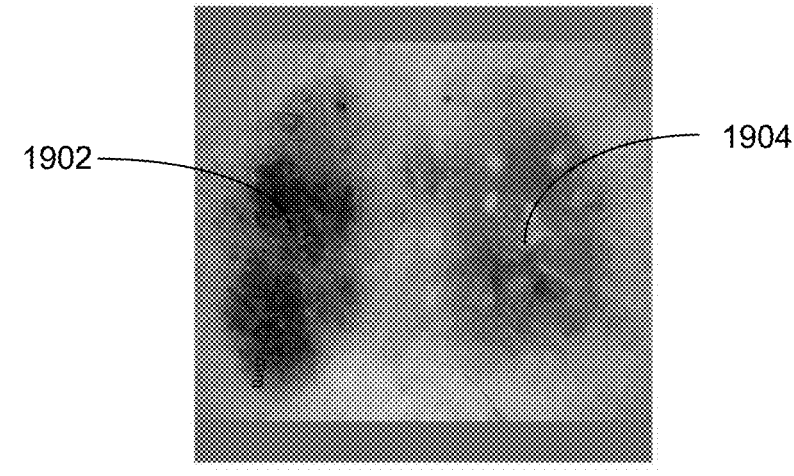
FIG. 19 is an example of skin cancer collision and the classification in an embodiment.

Referring now to FIG. 19, therein is shown an example of skin cancer collision 1901 and the classification in an embodiment. Skin lesion classification 520 of FIG. 5 is primarily of one class output. Very rarely collision cases can occur (383/100,000 images~0.38%). The XAI module 518 of FIG. 5 can be trained to predict at least two classes in this situation. The classification model 519 of FIG. 5 can identify the BCC 1902 and the BKL 1904

Figure 20:
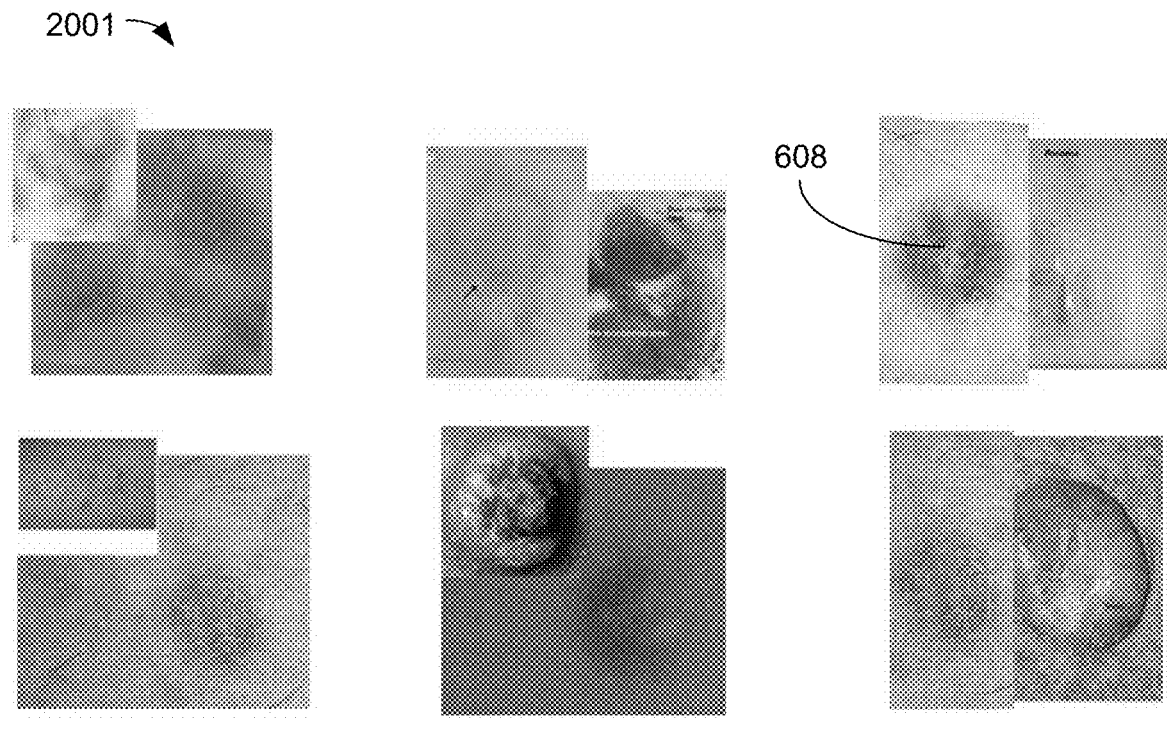
FIG. 20 is an example of a collision images of skin cancer collision for testing the explainable AI in an embodiment.

Referring now to FIG. 20, therein is shown an example of a collision images 2001 of skin cancer collisions for testing the XAI module 518 of FIG. 5 in an embodiment. These samples of diverse types of skin cancer have been created as a training and test case for the XAI module 518.

In order to train the XAI module 518, the manufacture of the collision images 2001 can combine two or more known skin conditions including the skin lesions 608. In processing the collision images 2001, the classification model 519 of FIG. 5 can identify more than one of the skin lesions 608 in each of the collision images 2001.

Referring now to FIG. 21 therein is shown an example of a skin lesion display 2101 of one half of the skin cancer collision 1901 of FIG. 19. The XAI module 518 of FIG. 5 is capable of isolating and analyzing the benign 316 lesions of the keratosis (BKL) 2102 separate from the melanoma (MEL) that is shown in an adjacent location in FIG. 19.

The skin lesion display 2101 depicts the risk level assessment 522 indicating no cancer risk from the BKL 2102. The skin lesion classification 520 identifies the skin lesion 608 in the normalized image 602 as the benign 316 lesions of the keratosis (BKL) 2102. The skin lesion display 2101 also provides the skin lesion sub-class 1404 indicating the possible sub-class of the BKL 2102. Optionally, the risk level assessment 522, the skin lesion classification 520, or a combination thereof can be displayed in the normalized image 602.

Referring now to FIG. 22, therein an example of a skin lesion display 2201 of a second half of the skin cancer collision 1901 of FIG. 19. The XAI module 518 of FIG. 5 is capable of isolating and analyzing the melanoma (MEL) separate from the BKL that is shown in an adjacent location in FIG. 19.

The skin lesion display 2201 depicts the risk level assessment 522 indicating significant cancer risk from the BCC or the MEL 2202. The skin lesion classification 520 identifies the skin lesion 608 in the normalized image 602 as the basal cell carcinoma (BCC) or the melanoma cancer (MEL) 2202. The skin lesion display 2201 also provides the skin lesion sub-class 1404 indicating the possible sub-class of the skin lesion 608. Optionally, the risk level assessment 522, the skin lesion classification 520, or a combination thereof can be displayed in the normalized image 602.

Figure 23:
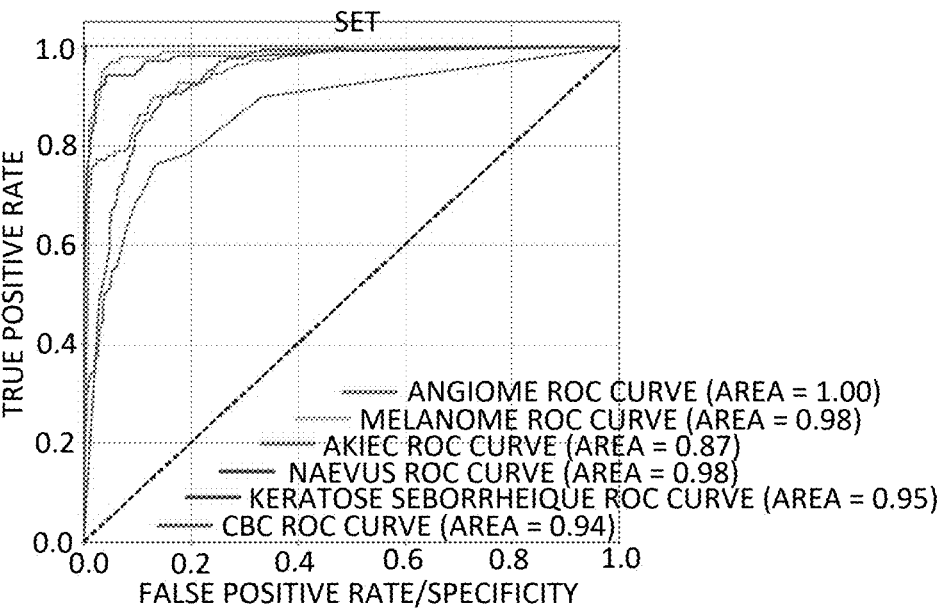
FIG. 23 is an example of a receiver operating characteristic (ROC) validation curve for each class of skin cancer identified in the 653 image test set.

Referring now to FIG. 23, therein is shown an example of a receiver operating characteristic (ROC) validation curve 2301 for each class of skin cancer identified in the 653 images of the Celine's test set. The ROC validation curve 2301 indicates the proficiency of the XAI module 518 of FIG. 5 in identifying the individual cancers represented in the Celine's test set used as a validation of the capabilities of cancer identification mechanisms.

Figure 24:
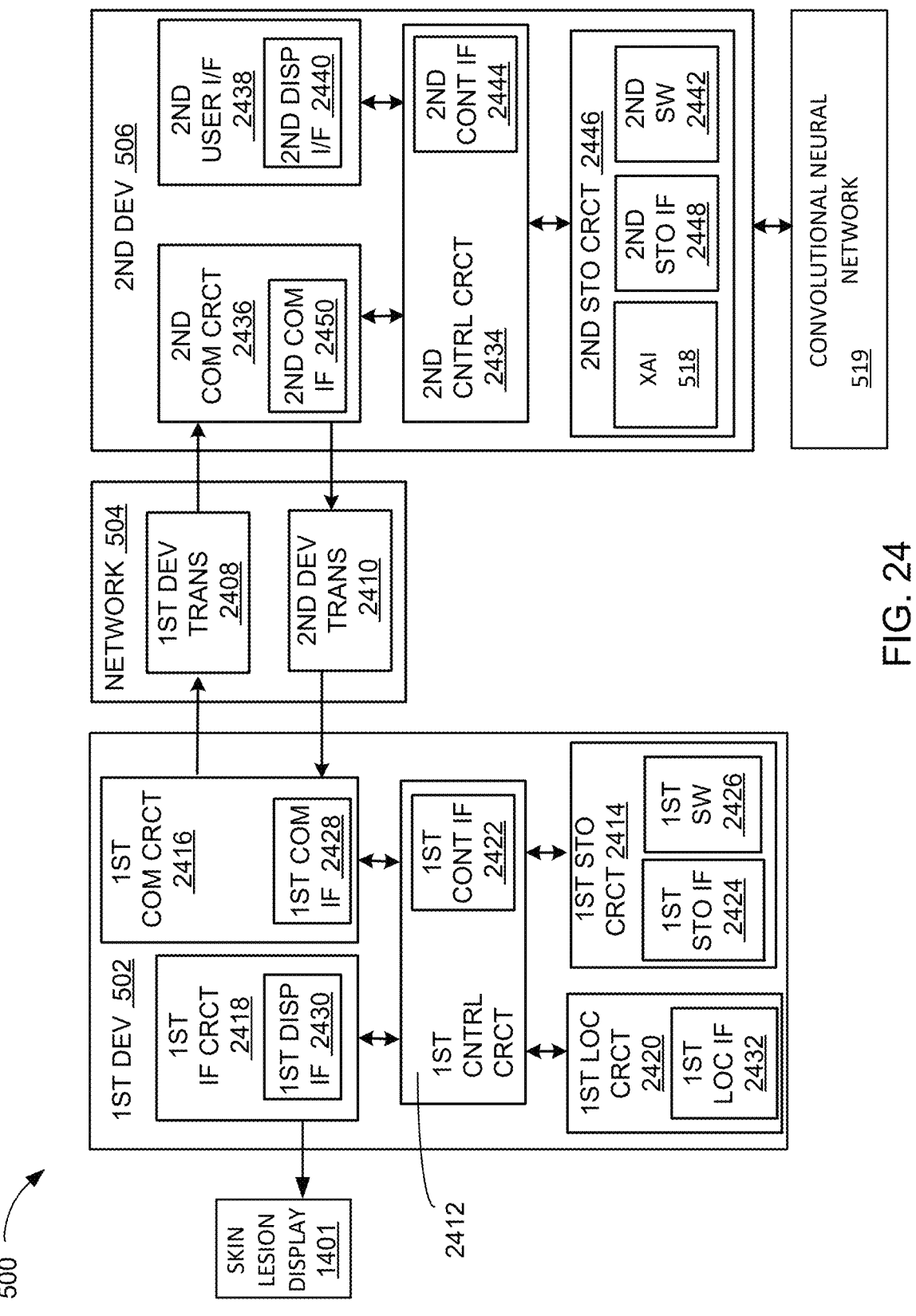
FIG. 24 is an exemplary block diagram of the compute system in an embodiment.

Referring now to FIG. 24, therein is shown an exemplary block diagram of the compute system 500 in an embodiment. The compute system 500 can include the first device 502, the network 504, and the second device 506. The first device 502 can send information in a first device transmission 2408 over the network 504 to the second device 506. The second device 506 can send information in a second device transmission 2410 over the network 504 to the first device 502.

For illustrative purposes, the compute system 500 is shown with the first device 502 as a client device, although it is understood that the compute system 500 can include the first device 502 as a different type of device.

Also, for illustrative purposes, the compute system 500 is shown with the second device 506 as a server, although it is understood that the compute system 500 can include the second device 506 as a different type of device. For example, the second device 506 can be a client device. By way of an example, the compute system 500 can be implemented entirely on the first device 502.

Also, for illustrative purposes, the compute system 500 is shown with interaction between the first device 502 and the second device 506. However, it is understood that the first device 502 can be a part of or the entirety of a cancer diagnostic device, a cancer analysis tool, or a combination thereof. Similarly, the second device 506 can similarly interact with the first device 502 representing the cancer diagnostic device, the cancer analysis tool, or a combination thereof.

For brevity of description in this embodiment of the present invention, the first device 502 will be described as a client device, and the second device 506 will be described as a server device. The embodiment of the present invention is not limited to this selection for the type of devices. The selection is an example of an embodiment of the present invention.

The first device 502 can include a first control circuit 2412, a first storage circuit 2414, a first communication circuit 2416, a first interface circuit 2418, and a first location circuit 2420. The first control circuit 2412 can include a first control interface 2422. The first control circuit 2412 can execute a first software 2426 to provide the intelligence of the compute system 500.

The first control circuit 2412 can be implemented in a number of different manners. For example, the first control circuit 2412 can be a processor, an application specific integrated circuit (ASIC) an embedded processor, a microprocessor, a hardware control logic, a hardware finite state machine (FSM), a digital signal processor (DSP), or a combination thereof. The first control interface 2422 can be used for communication between the first control circuit 2412 and other functional units or circuits in the first device 502. The first control interface 2422 can also be used for communication that is external to the first device 502.

The first control interface 2422 can receive information from the other functional units/circuits or from external sources, or can transmit information to the other functional units/circuits or to external destinations. The external sources and the external destinations refer to sources and destinations external to the first device 502.

The first control interface 2422 can be implemented in different ways and can include different implementations depending on which functional units/circuits or external units/circuits are being interfaced with the first control interface 2422. For example, the first control interface 2422 can be implemented with a pressure sensor, an inertial sensor, a microelectromechanical system (MEMS), optical circuitry, waveguides, wireless circuitry, wireline circuitry, or a combination thereof.

The first storage circuit 2414 can store the first software 2426. The first storage circuit 2414 can also store the relevant information, such as data representing incoming images, data representing previously presented image, sound files, or a combination thereof.

The first storage circuit 2414 can be a volatile memory, a nonvolatile memory, an internal memory, an external memory, or a combination thereof. For example, the first storage circuit 2414 can be a nonvolatile storage such as non-volatile random-access memory (NVRAM), Flash memory, disk storage, or a volatile storage such as static random-access memory (SRAM).

The first storage circuit 2414 can include a first storage interface 2424. The first storage interface 2424 can be used for communication between the first storage circuit 2414 and other functional units or circuits in the first device 502. The first storage interface 2424 can also be used for communication that is external to the first device 502.

The first storage interface 2424 can receive information from the other functional units/circuits or from external sources, or can transmit information to the other functional units/circuits or to external destinations. The external sources and the external destinations refer to sources and destinations external to the first device 502. The first storage interface 2424 can receive input from and source data to the XAI module 518.

The first storage interface 2424 can include different implementations depending on which functional units/circuits or external units/circuits are being interfaced with the first storage circuit 2414. The first storage interface 2424 can be implemented with technologies and techniques similar to the implementation of the first control interface 2422.

The first communication circuit 2416 can enable external communication to and from the first device 502. For example, the first communication circuit 2416 can permit the first device 502 to communicate with the second device 506 and the network 504.

The first communication circuit 2416 can also function as a communication hub allowing the first device 502 to function as part of the network 504 and not limited to be an endpoint or terminal circuit to the network 504. The first communication circuit 2416 can include active and passive components, such as microelectronics or an antenna, for interaction with the network 504.

The first communication circuit 2416 can include a first communication interface 2428. The first communication interface 2428 can be used for communication between the first communication circuit 2416 and other functional units or circuits in the first device 502. The first communication interface 2428 can receive information from the second device 506 for distribution to the other functional units/circuits or can transmit information to the other functional units or circuits.

The first communication interface 2428 can include different implementations depending on which functional units or circuits are being interfaced with the first communication circuit 2416. The first communication interface 2428 can be implemented with technologies and techniques similar to the implementation of the first control interface 2422.

The first interface circuit 2418 allows the user 512 of FIG. 5 to interface and interact with the first device 502. The first interface circuit 2418 can include an input device and an output device. Examples of the input device of the first interface circuit 2418 can include a keypad, a touchpad, soft-keys, a keyboard, a microphone, an infrared sensor for receiving remote signals, or any combination thereof to provide data and communication inputs.

The first interface circuit 2418 can include a first display interface 2430. The first display interface 2430 can include an output device. The first display interface 2430 can include a projector, a video screen, a touch screen, a speaker, a microphone, a keyboard, and combinations thereof.

The first control circuit 2412 can operate the first interface circuit 2418 to display information generated by the compute system 500 and receive input from the user 512. The first control circuit 2412 can also execute the first software 2426 for the other functions of the compute system 500, including receiving location information from the first location circuit 2420. The first control circuit 2412 can further execute the first software 2426 for interaction with the network 504 via the first communication circuit 2416. The first control circuit 2412 can operate the XAI module 518 of FIG. 5.

The first control circuit 2412 can also receive location information from the first location circuit 2420. The first control circuit 2412 can operate the XAI module 518.

The first location circuit 2420 can be implemented in many ways. For example, the first location circuit 2420 can function as at least a part of the global positioning system, an inertial compute system, a cellular-tower location system, a gyroscope, or any combination thereof. Also, for example, the first location circuit 2420 can utilize components such as an accelerometer, gyroscope, or global positioning system (GPS) receiver.

The first location circuit 2420 can include a first location interface 2432. The first location interface 2432 can be used for communication between the first location circuit 2420 and other functional units or circuits in the first device 502.

The first location interface 2432 can receive information from the other functional units/circuits or from external sources, or can transmit information to the other functional units/circuits or to external destinations. The external sources and the external destinations refer to sources and destinations external to the first device 502. The first location interface 2432 can receive the global positioning location from the global positioning system (not shown).

The first location interface 2432 can include different implementations depending on which functional units/circuits or external units/circuits are being interfaced with the first location circuit 2420. The first location interface 2432 can be implemented with technologies and techniques similar to the implementation of the first control circuit 2412.

The second device 506 can be optimized for implementing an embodiment of the present invention in a multiple device embodiment with the first device 502. The second device 506 can provide the additional or higher performance processing power compared to the first device 502. The second device 506 can include a second control circuit 2434, a second communication circuit 2436, a second user interface 2438, and a second storage circuit 2446.

The second user interface 2438 allows an operator (not shown) to interface and interact with the second device 506. The second user interface 2438 can include an input device and an output device. Examples of the input device of the second user interface 2438 can include a keypad, a touchpad, soft-keys, a keyboard, a microphone, or any combination thereof to provide data and communication inputs. Examples of the output device of the second user interface 2438 can include a second display interface 2440. The second display interface 2440 can include a display, a projector, a video screen, a speaker, or any combination thereof.

The second control circuit 2434 can execute a second software 2442 to provide the intelligence of the second device 506 of the compute system 500. The second software 2442 can operate in conjunction with the first software 2426. The second control circuit 2434 can provide additional performance compared to the first control circuit 2412.

The second control circuit 2434 can operate the second user interface 2438 to display information. The second control circuit 2434 can also execute the second software 2442 for the other functions of the compute system 500, including operating the second communication circuit 2436 to communicate with the first device 502 over the network 504.

The second control circuit 2434 can be implemented in a number of different manners. For example, the second control circuit 2434 can be a processor, an embedded processor, a microprocessor, hardware control logic, a hardware finite state machine (FSM), a digital signal processor (DSP), or a combination thereof.

The second control circuit 2434 can include a second control interface 2444. The second control interface 2444 can be used for communication between the second control circuit 2434 and other functional units or circuits in the second device 506. The second control interface 2444 can also be used for communication that is external to the second device 506.

The second control interface 2444 can receive information from the other functional units/circuits or from external sources, or can transmit information to the other functional units/circuits or to external destinations. The external sources and the external destinations refer to sources and destinations external to the second device 506.

The second control interface 2444 can be implemented in different ways and can include different implementations depending on which functional units/circuits or external units/circuits are being interfaced with the second control interface 2444. For example, the second control interface 2444 can be implemented with a pressure sensor, an inertial sensor, a microelectromechanical system (MEMS), optical circuitry, waveguides, wireless circuitry, wireline circuitry, or a combination thereof.

The second storage circuit 2446 can store the second software 2442. The second storage circuit 2446 can also store the information such as data representing incoming images, data representing previously presented image, sound files, or a combination thereof. The second storage circuit 2446 can be sized to provide the additional storage capacity to supplement the first storage circuit 2414.

For illustrative purposes, the second storage circuit 2446 is shown as a single element, although it is understood that the second storage circuit 2446 can be a distribution of storage elements. Also, for illustrative purposes, the compute system 500 is shown with the second storage circuit 2446 as a single hierarchy storage system, although it is understood that the compute system 500 can include the second storage circuit 2446 in a different configuration. For example, the second storage circuit 2446 can be formed with different storage technologies forming a memory hierarchal system including different levels of caching, main memory, rotating media, or off-line storage.

The second storage circuit 2446 can be a controller of a volatile memory, a nonvolatile memory, an internal memory, an external memory, or a combination thereof. For example, the second storage circuit 2446 can be a controller of a nonvolatile storage such as non-volatile random-access memory (NVRAM), Flash memory, disk storage, or a volatile storage such as static random access memory (SRAM).

The second storage interface 2448 can receive information from the other functional units/circuits or from external sources, or can transmit information to the other functional units/circuits or to external destinations. The external sources and the external destinations refer to sources and destinations external to the second device 506.

The second storage interface 2448 can include different implementations depending on which functional units/circuits or external units/circuits are being interfaced with the second storage circuit 2446. The second storage interface 2448 can be implemented with technologies and techniques similar to the implementation of the second control interface 2444.

The second communication circuit 2436 can enable external communication to and from the second device 506. For example, the second communication circuit 2436 can permit the second device 506 to communicate with the first device 502 over the network 504.

The second communication circuit 2436 can also function as a communication hub allowing the second device 506 to function as part of the network 504 and not limited to be an endpoint or terminal unit or circuit to the network 504. The second communication circuit 20 36 can include active and passive components, such as microelectronics or an antenna, for interaction with the network 504.

The second communication circuit 2436 can include a second communication interface 2450. The second communication interface 2450 can be used for communication between the second communication circuit 2436 and other functional units or circuits in the second device 506. The second communication interface 2450 can receive information from the other functional units/circuits or can transmit information to the other functional units or circuits.

The second communication interface 2450 can include different implementations depending on which functional units or circuits are being interfaced with the second communication circuit 2436. The second communication interface 2450 can be implemented with technologies and techniques similar to the implementation of the second control interface 2444.

The second communication circuit 2436 can couple with the network 504 to send information to the first device 502. The first device 502 can receive information in the first communication circuit 2416 from the second device transmission 2410 of the network 504. The compute system 500 can be executed by the first control circuit 2412, the second control circuit 2434, or a combination thereof. For illustrative purposes, the second device 506 is shown with the partition containing the second user interface 2438, the second storage circuit 2446, the second control circuit 2434, and the second communication circuit 2436, although it is understood that the second device 506 can include a different partition. For example, the second software 2442 can be partitioned differently such that some or all of its function can be in the second control circuit 2434 and the second communication circuit 2436. Also, the second device 506 can include other functional units or circuits not shown in FIG. 24 for clarity.

The functional units or circuits in the first device 502 can work individually and independently of the other functional units or circuits. The first device 502 can work individually and independently from the second device 506 and the network 504.

The functional units or circuits in the second device 506 can work individually and independently of the other functional units or circuits. The second device 506 can work individually and independently from the first device 502 and the network 504.

The functional units or circuits described above can be implemented in hardware. For example, one or more of the functional units or circuits can be implemented using a gate array, an application specific integrated circuit (ASIC), circuitry, a processor, a computer, integrated circuit, integrated circuit cores, a pressure sensor, an inertial sensor, a microelectromechanical system (MEMS), a passive device, a physical non-transitory memory medium containing instructions for performing the software function, a portion therein, or a combination thereof.

For illustrative purposes, the compute system 500 is described by operation of the first device 502 and the second device 506. It is understood that the first device 502 and the second device 506 can operate any of the modules and functions of the compute system 500.

Figures 25, 26:
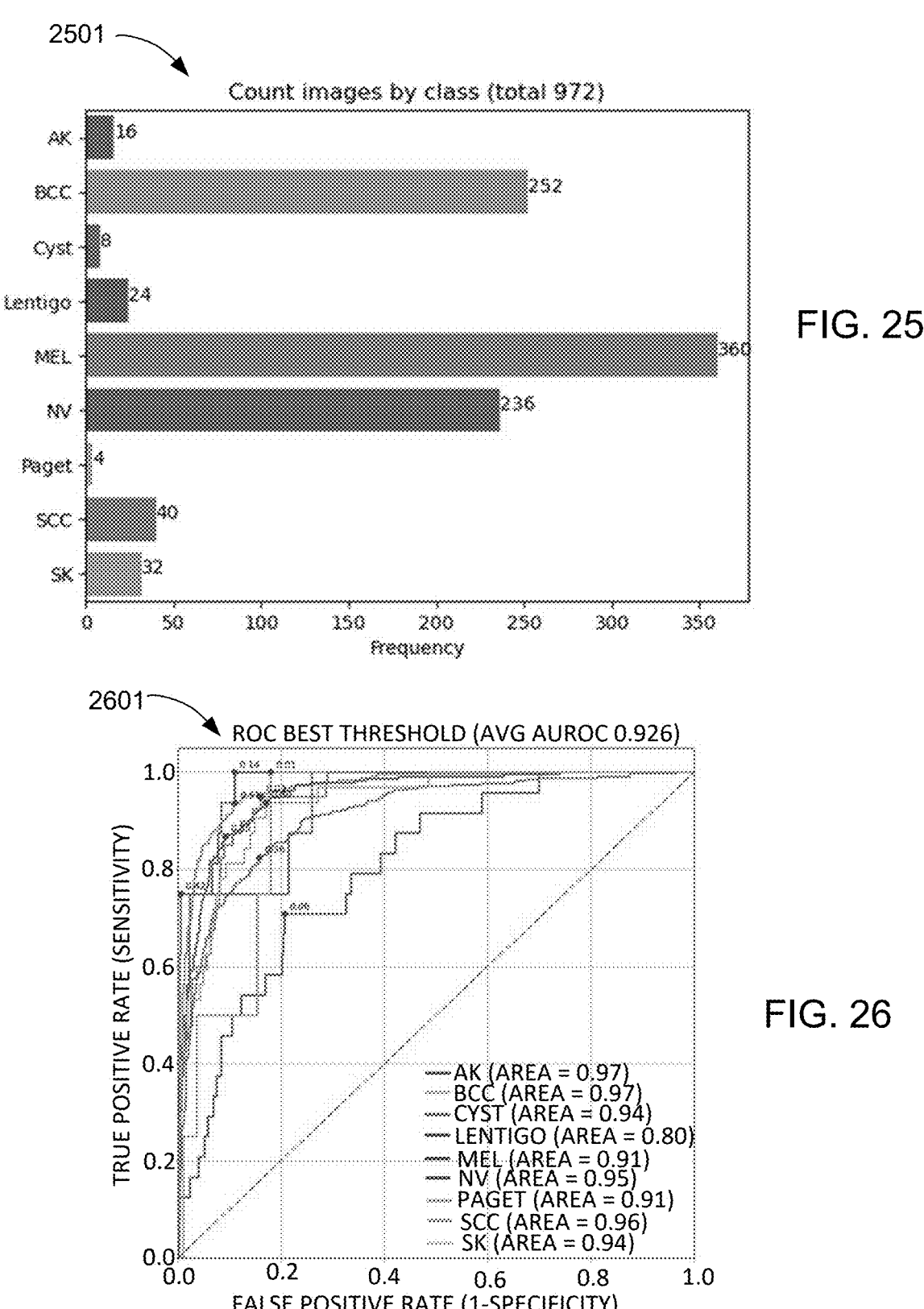
FIG. 25 is an exemplary bar chart of an AUROC curve for the prediction of the explainable AI.
FIG. 26 is an exemplary receiver operating characteristic (ROC) validation curve of sensitivity of the explainable AI.

Referring now to FIG. 25, therein is shown an exemplary bar chart 2501 of an AUROC curve for the prediction of the XAI module 518 of FIG. 5.

Referring now to FIG. 26, therein is shown an exemplary receiver operating characteristic (ROC) validation curve 2601 of sensitivity of the XAI module 518 of FIG. 5.

Figure 27:
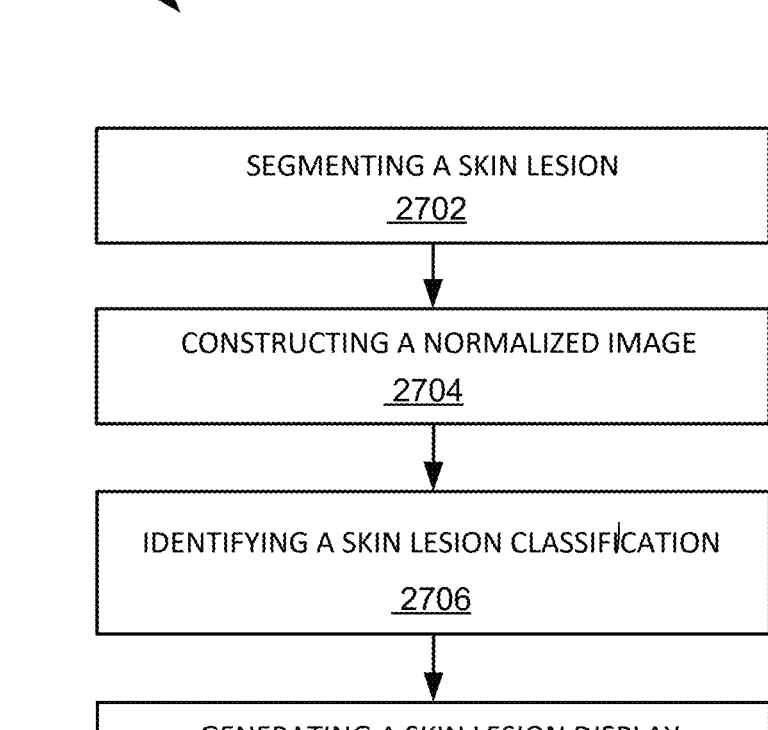
FIG. 27 is a flow chart of a method of operation of a compute system in an embodiment of the present invention.

Referring now to FIG. 27, therein is shown is a flow chart of a method of operation 2700 of a compute system 500 in an embodiment of the present invention. The method 2700 includes: segmenting a skin lesion in a patient image in a block 2702; constructing a normalized image by cropping the patient image and adding padding to position the skin lesion at the center of the normalized image in a block 2704; identifying a skin lesion classification, a skin lesion sub-class, and a risk level assessment by analyzing a symmetry axis, a border, color variation, and dermoscopic structures in a block 2706; and generating a skin lesion display including the normalized image, the skin lesion classification, the skin lesion sub-class, and the risk level assessment for displaying on a device in a block 2708.

The resulting method, process, apparatus, device, product, and/or system is straightforward, cost-effective, uncomplicated, highly versatile, accurate, sensitive, and effective, and can be implemented by adapting known components for ready, efficient, and economical manufacturing, application, and utilization. Another important aspect of an embodiment of the present invention is that it valuably supports and services the historical trend of reducing costs, simplifying systems, and increasing performance.

These and other valuable aspects of an embodiment of the present invention consequently further the state of the technology to at least the next level.

While the invention has been described in conjunction with a specific best mode, it is to be understood that many alternatives, modifications, and variations will be apparent to those skilled in the art in light of the foregoing description. Accordingly, it is intended to embrace all such alternatives, modifications, and variations that fall within the scope of the included claims. All matters set forth herein or shown in the accompanying drawings are to be interpreted in an illustrative and non-limiting sense.

What is claimed is:

1. A method of operation of a compute system comprising:

segmenting a skin lesion in a patient image, which is an uploaded image accepted based on a photo guideline;

constructing a normalized image by cropping the patient image and adding padding to position the skin lesion at a center of the normalized image;

identifying a skin lesion classification, a skin lesion sub-class, and a risk level assessment by analyzing a symmetry axis, a border, color variation, and dermoscopic structures, wherein a potential malignancy is determined by a discrepancy between a convex hull and the border of the skin lesion; and generating a skin lesion display including the normalized image, the skin lesion classification, the skin lesion sub-class, and the risk level assessment for displaying on a device.

2. The method as claimed in claim 1 further comprising predicting a medical element by calculating a total loss (EQ2) to establish a confidence of accuracy of the skin lesion classification.

3. The method as claimed in claim 1 further comprising predicting a medical element including a pigment network, a streak, pigmentation, a regression structure, dots and globules, a blue whitish veil, a vascular structure, or a combination thereof.

4. The method as claimed in claim 1 further comprising generating a negative grayscale format by replacing pixel intensities based on background intensity (EQ1) to assess asymmetry, the border, the color variation, and the dermoscopic structure of the skin lesion.

5. The method as claimed in claim 1 further comprising assessing a difference between the border and the convex hull, wherein the assessing includes a highlight showing asymmetry of the skin lesion.

6. The method as claimed in claim 1 further comprising identifying as malignant the skin lesion based on a low number of symmetry axes.

7. The method as claimed in claim 1 further comprising identifying as benign the skin lesion based on a low number of colors.

8. A compute system comprising:

a control circuit, including a processor, configured to:

segment a skin lesion in a patient image, which is an uploaded image accepted based on a photo guideline;

construct a normalized image by cropping the patient image and adding padding to position the skin lesion at the center of the normalized image;

identify a skin lesion classification, a skin lesion sub-class, and a risk level assessment by analysis of a symmetry axis, a border, color variation, and dermoscopic structures, wherein a potential malignancy is determined by a discrepancy between a convex hull and the border of the skin lesion; and generate a skin lesion display including the normalized image, the skin lesion classification, the skin lesion sub-class, and the risk level assessment for displaying on a device.

9. The system as claimed in claim 8 wherein the control circuit is configured to predict a medical element by calculating a total loss (EQ2) to establish a confidence of accuracy of the skin lesion classification.

10. The system as claimed in claim 8 wherein the control circuit is configured to predict a medical element including a pigment network, a streak, pigmentation, a regression structure, dots and globules, a blue whitish veil, a vascular structure, or a combination thereof.

11. The system as claimed in claim 8 wherein the control circuit is further configured to generate a negative grayscale format by replacing pixel intensities based on background intensity (EQ1) to assess asymmetry, the border, the color variation, and the dermoscopic structure of the skin lesion.

12. The system as claimed in claim 8 wherein the control circuit is further configured to assess a difference between the border and the convex hull, wherein the assessment includes a highlight showing asymmetry of the skin lesion.

13. The system as claimed in claim 8 wherein the control circuit is further configured to identify as malignant the skin lesion based on a low number of symmetry axes.

14. The system as claimed in claim 8 wherein the control circuit is further configured to identify as benign the skin lesion based on a low number of colors.

15. A non-transitory computer readable medium including instructions for a compute system which, when executed by a processor, cause the processor to execute the instructions comprising:

segmenting a skin lesion in a patient image, which is an uploaded image accepted based on a photo guideline;

constructing a normalized image by cropping the patient image and adding padding to position the skin lesion at a center of the normalized image;

identifying a skin lesion classification, a skin lesion sub-class, and a risk level assessment by analyzing a symmetry axis, a border, color variation, and dermoscopic structures, wherein a potential malignancy is determined by a discrepancy between a convex hull and the border of the skin lesion; and generating a skin lesion display including the normalized image, the skin lesion classification, the skin lesion sub-class, and the risk level assessment for displaying on a device.

16. The non-transitory computer readable medium as claimed in claim 15 further comprising predicting a medical element by calculating a total loss (EQ2) to establish a confidence of accuracy of the skin lesion classification.

17. The non-transitory computer readable medium as claimed in claim 15 further comprising predicting a medical element including a pigment network, a streak, pigmentation, a regression structure, dots and globules, a blue whitish veil, a vascular structure, or a combination thereof.

18. The non-transitory computer readable medium as claimed in claim 15 further comprising generating a negative grayscale format by replacing pixel intensities based on background intensity (EQ1) to assess asymmetry, the border, the color variation, and the dermoscopic structure of the skin lesion.

19. The non-transitory computer readable medium as claimed in claim 15 further comprising assessing a difference between the border and the convex hull, wherein the assessing includes a highlight showing asymmetry of the skin lesion.

20. The non-transitory computer readable medium as claimed in claim 15 further comprising identifying as malignant the skin lesion based on a low number of symmetry axes.

*     *     *     *     *